(12) United States Patent
Cahoon et al.

(10) Patent No.: US 7,199,284 B2
(45) Date of Patent: Apr. 3, 2007

(54) CHLOROPHYLLASES

(75) Inventors: Edgar B. Cahoon, Wilmington, DE (US); Rebecca E. Cahoon, Wilmington, DE (US); Catherine J. Thorpe, St. Albans (GB)

(73) Assignee: E. I. du Pont de Nemours and Company, Wilmington, DE (US)

( * ) Notice: Subject to any disclaimer, the term of this patent is extended or adjusted under 35 U.S.C. 154(b) by 680 days.

(21) Appl. No.: 10/381,123

(22) Filed: Mar. 21, 2003

(65) Prior Publication Data

US 2005/0081263 A1  Apr. 14, 2005

Related U.S. Application Data

(60) Provisional application No. 60/238,161, filed on Oct. 5, 2000.

(51) Int. Cl.
*C12N 15/29* (2006.01)
*C12N 15/52* (2006.01)
*C12N 15/82* (2006.01)
*A01H 5/00* (2006.01)
*A01H 5/10* (2006.01)

(52) U.S. Cl. ............... 800/298; 800/282; 536/23.2; 536/23.6; 435/320.1; 435/419

(58) Field of Classification Search ............... 800/278, 800/282, 287, 298; 536/23.1, 23.2, 23.6; 435/419, 320.1
See application file for complete search history.

(56) References Cited

OTHER PUBLICATIONS

Jacob-Wilk D. et al. The Plant Journal, 1999; vol. 20, No. 6, pp. 653-661.*
Benedetti C. et al. Plant Physiology, Apr. 2002, vol. 128. pp. 1255-1263.*
Tsuchiya T. et al. PNAS, Dec. 21, 1999; vol. 96, No. 26 pp. 15362-15367.*
National Center for Biotechnology Information General Identifier No. 6914327, Accession No. AW395857, Feb. 7, 2000, R. Shoemaker, Public Soybean Est Project.
National Center for Biotechnology Information General Identifier No. 7284173, Accession No. AW596770, Mar. 22, 2000. R. Shoemaker, Public Soybean Est Project.
National Center for Biotechnology Information General Identifier No. 7328567, Accession No. AAF59834, Mar. 25, 2000, Jacob-Wilk, D. et al., Chlorophyll breakdown by chlorophyllase: isolation and functional expression of the Chlase1 gene from ethylene-treated Citrus fruit and its regulation during development.
National Center for Biotechnology Information General Identifier No. 6729675, Accession No. AAF27045, Jan. 22, 2000, T. Tsuchiya et al., Cloning of chlorophyllase, the key enzyme in chlorophyll degradation: finding of a lipase motif and the induction by methyl jasmonate.
National Center for Biotechnology Information General Identifier No. 6729677, Accession No. AAF27046, Jan. 22, 2000, T. Tsuchiya et al., Cloning of chlorophyllase, the key enzyme in chlorophyll degradation: finding of a lipase motif and the induction by methyl jasmonate.
National Center for Biotechnology Information General Identifier No. 2460203, Accession No. AAC13947, Apr. 17, 1998, C.E. Benedetti et al., Differential expression of a novel gene in response to corronatine, methyl jasmonate, and wounding in the Coli mutant of Arabidopsis.
Tsuchiya, T. et al., Cloning of chlorophyllase, the key enzyme in chlorophyll degradation: Finding of a lipase motif and the induction by methyl jasmonate, PNAS, vol. 96(26):15362-15367, Dec. 1999, XP002208646.
Jacob-Wilk, D. et al., Chlorophyll breakdown by chlorophyllase: isolation and functional expression of the Chase1 gene from ethylene-treated Citrus fruit and its regulation during development, The Plant Journal, vol. 20(6):653-661, Dec. 1999, XP002208647.
Takamiya, K. et al., Degradation pathway(s) of chlorophyll: what has gene cloning revealed?, Trends in Plant Science, vol. 5(10):426-431, Oct. 2000, XP002208648.
Benedetti Celso E. et al., Differential expression of a novel gene in response to coronatine, methyl jasmonate, and wounding in the Coil mutant of arabidopsis, Plant Phys., vol. 116(3):1037-1042, Mar. 1998, XP002146876.
Trebitsh, T. et al., Ethylene induces de novo synthesis of chlorophyllase, a chlorophyll degrading enzyme, in Citrus fruit peel, PNAS, vol. 90:9441-9445, Oct. 1993, XP002208649.
K. Takamiya et al., Degradation pathway(s) of chlorophyll: what has gene cloning revealed?, Trends in Plant Science, vol. 5, No. 10, pp. 1380-1385, Oct. 2000.
K. A.J. Arkus et al., Mechanistic analysis of what chlorophyllase, Archives of Biochemistry and Biophysics, vol. 438, pp. 146-165, 2005.
C. E. Benedetti et al., Altering the Expression of the Chlorophyllase Gene *ATHCOR1* in Transgenic Arabidopsis Caused Changes in the Chlorophyll-to-Chlorophyllide Ratio, Plant Physiology, vol. 128, pp. 1256-1263, Apr. 2002.

* cited by examiner

*Primary Examiner*—Russell P. Kallis

(57) ABSTRACT

This invention relates to isolated polynucleotides encoding chlorophyllases. The invention also relates to the construction of recombinant DNA fragments comprising all or a portion of the isolated chlorophyllase-encoding polynucleotides, in sense or antisense orientation, wherein expression of the recombinant DNA fragment results in production of altered levels of chlorophyllase in a transformed host cell.

14 Claims, 8 Drawing Sheets

```
SEQ ID NO:19  MAAIEDSPTFSS---VVTPAA------------------------FEIGSLPTTEIPVDPV------------ENDST
SEQ ID NO:20  MS-SSSSR--------------------------------------------------------NAFEDGKYKSNLLTLD---SSSRCCKITPSSRASP
SEQ ID NO:22  MAAMVDAKPAAS---VQGTPLLA----------------------TATLPVFTRGIYSTKRITLETSSPS------------SP
SEQ ID NO:21  MAKLLLIFGVFIFVNSQAQTFPTILEKHNSEKITDVFHKGNFQVTNNPI-----------RVKRYEF
SEQ ID NO: 2  ----------------------------------------------------------------RVET------SNIA-
SEQ ID NO: 4  STCSTTAA-------------------------------------NVFEIGKHITVLLRAE---PGT--C--TTKSSLPV
SEQ ID NO: 6  MNLASAVRVFLSYYLLVQRWMGS----------------EQGGGVFDQGGHSVSLTRLDEARAPPRCAVRSSPSSAAS
SEQ ID NO: 8  MAQRAEPILVT---------------------------------TDVFQMGNIKWKQFNIDT------------SNASS
SEQ ID NO:10  MAQRAQPVLAT---------------------------------DVFQMGNIQWKQFNVDT-------------SSASF
SEQ ID NO:12  MAQRAQPALAT---------------------------------TDVFQKGDIHWKQFNVET-------------STASS
SEQ ID NO:14  MASSPCS-------------------------------------VFVPGKYTVQLKSVE---AGTK--KARHVSSVSA
SEQ ID NO:16  MAAAAPAETMNK---SAAGAEVP---------------------EAFTSVFQPGKLAVEAIQVDE----------NAAP
SEQ ID NO:18  MAAMA-----------------------------------------TTVFQAGPMEVDVKHVDK----------SMIP
              1                                                                            70
```

FIG. 1A

```
SEQ ID NO:19   APPKPVRITCPTVAGTYPVVLFFHGFYLRNYFYSDVLNHIASHGYILVAPQLCKLLPP--GGQ-VEVDDA
SEQ ID NO:20   SPPKQLLVATPVEEGDYPVVMLLHGYLLYNSFYSQLMLHVSSHGFILIAPQLYSIAGP--DTM-DEIKST
SEQ ID NO:22   PPPKPLLIIVTPAGKGTFNVILFLHGTSLSNKSYSKIFDHIASHGFIVVAPQLYTSIPPP-SAT-NELNSA
SEQ ID NO:21   SAPEPLIIISPKEAGVYPVLLFIHGTMLSNEDYSLFFNYIASHGFIVVAPKLFRLFPPKLPSQQDEIDMA
SEQ ID NO:2    SPPKPLLIVTPTIQGTYPVLFLHGFELRNTFYTQLLQLISSHGFIVVAPQLYGLLPP--SGI-QEIKSA
SEQ ID NO:4    PPPLQLLIATPSEAGEFPLLLLLHGYLLYNSFYSQLIQHIASHGFIVLAPQLYTVAGP--DSS-EEIKSA
SEQ ID NO:6    LPPKPLLVAAPRETGEYPVILFLHGYLAVNSFYSQLFEHVASHGFIVVGPQLYTISGA--DTT-EEINSA
SEQ ID NO:8    SPPKPLLIFTPTVPGSYPVILFCHGFSLRNSYYSELIGHIASHGFIIVAPQLCWSVRSMLEPG-DEVKFA
SEQ ID NO:10   SPPKPLLIFTPTVPGAYPVILFVHGFFIRNFYYSKLLAHIVSHGFIIVAPQLFSNGLPMYGP--TEVEYA
SEQ ID NO:12   SPPKPLLIFTPTVPGLYPVILFCHGFCIRTSYYSKLLAHIVSHGFILVAPQLFSIGVPMFGP--EEVKCE
SEQ ID NO:14   PPRKPPLIATPFEEGEYPTLLLLHGEMLHNTFYSELIQHIASHGFIVVPQLYLVATC--DST-NGIKSA
SEQ ID NO:16   ----------------------------------------------------------------------
SEQ ID NO:18   TPPIPVLIVAPKDAGTYPVAMLLHGFFLNHFYEHLLRHVASHGFIIVAPQ-FSISIIPSGDA-EDIAAA
SEQ ID NO:26   NLARPLMVVAPKETGAYPVIVFLHGWNMLNSWYEQLLTHVASHGFIAVAPQLYWMVSEP--DA-DDIDAT
               71                                                                  140
```

FIG. 1B

```
                             *             *              *  **         * **   *          *
SEQ ID NO:19     GSVINW-ASE--NLKAHLPT------SVNANGKYTSLVGH  S  RGGKTAFAVALGHAAT-LDPSITFSALIGI
SEQ ID NO:20     AEIMDWLSV---GLNHFLPA------QVTPNLSKFALSGH  S  RGGKTAFAVALKKFGY-S-SNLKISTLIGI
SEQ ID NO:22     AEVAEWLPQ---GLQQNLPE------NTEANVSLVAVMGH  S  RGGQTAFALSLRYG--------FGAVIGL
SEQ ID NO:21     ASVANWMPLY--LQVVLQRYVT--GVEGDLEKLAISGH    S  RGGKSAFALALGFSNIK--LDVTFSALIGV
SEQ ID NO: 2     AAVTNWLSS---GLQSVLPE------NVKPDLLKLALSGH  S  RGGKTAFALALGYADT----SLNFSALLGL
SEQ ID NO: 4     AALTNWLSK---GLHDLLPP------HVRPNLSKLGLAGH  S  RGGKTAFALALRK--A-S-TSLKFSALIGI
SEQ ID NO: 6     AAVIDWLAT---GLPSTLPL------GVRANLTKVSISGH  S  RGGKVAFALALGH-AK-AKLAVPLAAVVAV
SEQ ID NO: 8     GKVVDWLAEE--GLQPLLPE------NVEAKLDKLVLSGH  S  KGGKTVFEAVALGYAKT----NLKFSALVGI
SEQ ID NO:10     GKVADWI-AE--ELQHLLPE------NVEANLDKLVLSGH  S  RGGKTVFEAVALGHAKT----NLKFSALVGI
SEQ ID NO:12     GRVVDWL-DN--GLQPLLPE------SVEAKLEKLVLVGH  S  KGGKTAFAVALGYCKT----KLKFSALIGI
SEQ ID NO:14     AKTTDWLKD---GLQDVLPT------KVRPDLKKIGLSGH  S  RGGKDAFALAL---GY-AKTTLSFSALIGV
SEQ ID NO:16     -----------------------PRVEPDLSKLALAGH    S  RGGQTAFAVALGLGDAKTKLELKFSALIGV
SEQ ID NO:18     AKVADWLP-D--GLPSVLPK------GVEPELSKLALAGL  S  RGGHTAFSLALGHAKT----QLTFSALIGL
SEQ ID NO:26     KRITNWLADHDKGLAHVLKDVLKEHVEPDLSKLALAGH    S  RGGQTAFAVALGLGDAKTKLELKFSALIGV
                141                                                                      210
```

FIG. 1C

```
            *** *                        *                     * * ***    * ***
SEQ ID NO:19    DPVAGTNKY--IRTDPHILTYKPESFELDI-PVAVVGTGLGP-KWNNVMPPCAPTDLNHEEFYKE--CKA
SEQ ID NO:20    DPVDGTGKGK--QTPPPVLAYLPNSFDLDKTPILVIGSGLGETARNPLFPPCAPPGVNHREFFRE--CQG
SEQ ID NO:22    DPVAGTSKTTG--LDPSILSF--DSFDFSI-PVTVIGTGLGGVAR--CITACAPEGANHEEFFNR--CKN
SEQ ID NO:21    DPVAG--RSVDDRTLPHVLTYKPNSFNLSI-PVTVIGSGLGNHTIS----CAPNHVSHQQFYDE--CKE
SEQ ID NO: 2    DPVGGLSKC--CQTVPKILTYVPHSFNLAI-PVCVIGTGLGDEPRNCLTCPCAPDGVNHVEFFSE--CKP
SEQ ID NO: 4    DPVDGMDKGK--QTPPPVLTYVPHSFDLDMA-VMVIGSGLGEVKRNPLFPPCAPKGVNHEDFFKE--CRE
SEQ ID NO: 6    DPVDGMGVGK--QTPPPILTGRHGSLHVG-APAMVIGTGLGELPRGSLLPPCAPRGVSHAAFYDELDGAA
SEQ ID NO: 8    DPVAGP--CKSCETFPPILTGMSQSFNLNI-PIVVIGTGLGPEKANFFIPPCAPDGVNHKEFFNK--CKP
SEQ ID NO:10    DPVAGTSKY--CRTRPHILTGKPRSFDLKM-PVEVIGTGLGPEKLNCCTPPCAPDGVNYKEFFNE--CKP
SEQ ID NO:12    DPVAGVSKCKPCRSLPDILTGVPRSFNLNI-PVAVIGTGLGPEKANSLFPPCAPNGVNHKEFFSE--CKP
SEQ ID NO:14    DPVDGVRKGH--QTNPPVLNYIPHSLELKM-PSLVIGTGLGELKRN-LFA-CAPKGVNHQDFYDE--CSS
SEQ ID NO:16    DPVAGVSRAQ--QLEPKVLTFEPDCLDVGM-PVLVMGTGLGPKHIGGF--PCAPVGVNHAEFYKE--CAP
SEQ ID NO:18    DPVAGTGK--SSQLQPKILTYEPSSFGMAM-PVLVIGTGLGEEKKNIFFPPCAPKDVNHAEFYRE--CRP
SEQ ID NO:26    DPVAGVSRAQ--QLEPKVLTFEPDCLDVGM-PVLVMGTGLGPKHIGGF--PCAPVGVNHAEFYKE--CAP
                211                                                             280
```

FIG. 1D

```
                   *** * **                    *                        *         *   **
SEQ ID NO:19   281 TK-AHFVAADYGHMDMLDDDLPGFVG-FMAGCMCKNGQR-KKSEMRSFVGGIVVAFLKYSLWGEKAEIRL 350
SEQ ID NO:20       PA-WHFVAKDYGHLDMLDDTKGIRG-KSSYCLCKNGEE--RRPMRRFVGGLVVSFLKAYLEGDDRELVK
SEQ ID NO:22       SSRAHFVATDYGHMDILDDNPSDVKSWALSKYFCKNGNES-RDPMRRCVSGIVVAFLKDFFYGDAEDFRQ
SEQ ID NO:21       NSS-HFVITKYGHMDMLNEFRLSPIAVTMSL-MCAQSFR-PKATMRRTLGGIMVAFLNAYFRDDGRQYYA
SEQ ID NO: 2       PC-SHFVTTEYGHLDMLDDHLSGCIGAI-SGYICKSGK-GPRDPMRRCVGGLFVAFLKAYLEGQTGDFKA
SEQ ID NO: 4       PA-CYFLAKDYGHLDMLDDETNGIRG-KATHCLCKNGKS--REPMRRFVGGIVIAFMKAYLEGDNSSLIS
SEQ ID NO: 6       PA-CHLVVRDYGHTDMDDDTPGARG-MLTRTICRSGGA--RAPMRRFVAGATVAFLKKWVAGDAAAMDS
SEQ ID NO: 8       PC-AHFVATEYGHMDMLDDVTPGLIGSILSNCICKDGK-GPRDLMRRTVGGLVVAFLVVSFLRAQLNGLWKDENA
SEQ ID NO:10       PC-AKFVVAKDYGHMDMLNDDTPGLIGTLVSKCMCKNGTTGPRDLMRRTTGGLVVSFLRAQLNDLWKDEDA
SEQ ID NO:12       PS-AYFVATDYGHMDMLDDETPGVIGTMMSKCMCKNGKKGPRDLMRRTVGGLVVAFLRAQLNEQWKDFDA
SEQ ID NO:14       PS-CHFVAKDYGHMDMLDDHTDGPRG-IVSYCMCRNGES--RTPMRLFVGGIVVAFLKACLQGDKQDLRA
SEQ ID NO:16       PR-YHLVVKDYGHLDMLDMLDDNVP----YIINNCMCMRNQHDTKDLARRTMGGAMVAFLRAKLRIDVRDLIA
SEQ ID NO:18       PC-YYFVTKDYGHLDMLDDDAPKFI----TCVCKDGN-GCKGKMRRCVAGIMVAFLNAALGEKDADLEA
SEQ ID NO:26       PR-YHLVVKDYGHLDMLDMLDDNVP----YIINNCMCMRNQHDTKDLARRTMGGAMVAFLRAKLRIDVRDLIA 350
```

FIG. 1E

```
SEQ ID NO:19    IVKD-PSVSPAKLDPSPELEEASGI----F-----------------------V
SEQ ID NO:20    IKDGCHEDVPVEIQEFEVI--------------------------------M
SEQ ID NO:22    ILKD-PSFAPIKLDSVEYIDASSMLTT-----------------THVKV
SEQ ID NO:21    I------IANRSLAPTNLFAEKKGFNFGF-------ATTYA-----QL
SEQ ID NO: 2    IVDE-PDLAPVKLDPVEFIEA------------------------------
SEQ ID NO: 4    IRDG-HATAPVELQNVEFL--------------------------------V
SEQ ID NO: 6    ITAR-PDQAPVALSVVEF----------------------GDEKAIA
SEQ ID NO: 8    VLAN-PNLAPTKLDDVVYVPA------------------------------
SEQ ID NO:10    ILKD-PNLAPTEVDGVDYIPA------------------------------
SEQ ID NO:12    ILAS-PNLAPAKLDDVRYLPT------------------------------
SEQ ID NO:14    LKDN-PEISNINLSIVDFYDPDGTLTKYFDGGSISTPHYAVQESHQQ
SEQ ID NO:16    IYHN-PEIAPAVLDQVDEFLP--------CFVGRPNPSS-------V
SEQ ID NO:18    ILRD-PAVAPTTLDPVEHRVA------------------------------
SEQ ID NO:26    IYHN-PEIAPAVLDQVDEFLP--------CFVGRPNPSS-------V
                351                                              397
```

FIG. 1F

```
SEQ ID NO:19   MAAI---------EDSPTFSSVVTPAAFEIGSLP---------TTEIPVDPVENDSTAPPKPVRITCP
SEQ ID NO:20   MSSS---------SSRNAFEDGKYKSNLLTLDSS--------SRCCKITPSSRASPSPPKQLLVATP
SEQ ID NO:22   MAAM---------VDAKPAASVQGTPLLATATLPVFTRGIYSTKRITLETSSPSSPPPPKPLIIVTP
SEQ ID NO:21   MAKLLLLIFGVEIFEVNSQAQTFPTILEKHNSEKIT-DVFHKGNFQVTNNPI-RVKRYEFSAPEPLIIISP
SEQ ID NO:28   MAAS---------P------------VAIGTAVFQRGPLRVEARHVD--YSQVPSVPKPLMVVAP
                                                                                *
                1                                                                70

SEQ ID NO:19   TVAGTYPVVLFFHGFYLRNYFYSDVLNHIASHGYILVAPQLCK-LLP--PGGQVEVDDAGSVINWAS----
SEQ ID NO:20   VEEGDYPVVMLLHGYLLYNSFYSQLMLHVSSHGFILIAPQLYS-IAG--PDTMDEIKSTAEIMDWLS----
SEQ ID NO:22   AGKGTENVILFLHGTSLSNKSYSKIFDHIASHGFIVVAPQLYTSIPP--PSATNELNSAAEVAEWLP----
SEQ ID NO:21   KEAGVYPLLFIHGTMLSNEDYSLFFNYIASHGFIVVAPKLFRLFPPKLPSQQDEIDMAASVANWMP----
SEQ ID NO:28   TDAGVYPVAVFLHGCNTVNSWYESLLSHVASHGFIAVAPQLYCVTLN--MNDLKDIDATRQVTAWLADKQ
                     *    **     *   *        * *  *                 *
                71                                                               140

SEQ ID NO:19   ENLKAHLPT------SVNAN-GKYTSLVGH  S  RGGKTAFAVALGHAATLDPS----------ITF
SEQ ID NO:20   VGLNHFLPA------QVTPNLSKFA-LSGH  S  RGGKTAFAVAL-KKFGYSSN----------LKI
SEQ ID NO:22   QGLQQNLPE------NTEANVS-LVAVMGH  S  RGGQTAFALSL--------R----------YGF
SEQ ID NO:21   ---LYLQVVLQRYTGVEGDLEKL-AISGH  S  RGGKSAFALALGF-------------SNIKLDVTF
SEQ ID NO:28   QGLAHVLANILQ--LHGVRPDLSRL-ALAGH  S  RGDTAFAVALGLGPAASDDDDNNADAGTSPAALPLKF
                                    *  ***   ***
                121                                                               180
```

FIG. 2A

```
                  *  *  ***  *                        *                       *                    * *   *
SEQ ID NO:19      SALIGIDPVAGTNKYIRTDPHILTYKPESFELD-IPVAVVGTLGPK-WNNVMPPCAPTDLNHEEFYKEC
SEQ ID NO:20      STLIGIDPVDGTGKGKQTPPVLAYLPNSFDLDKTPILVIGSLGETARNPLFPPCAPPGVNHREFREC
SEQ ID NO:22      GAVIGLDPVAGTSKTTGLDPSILSF--DSFDFS-IPVTVIGTLGGVARC---ITACAPEGANHEEFFNRC
SEQ ID NO:21      SALIGVDPVAGRSVDDRTLPHVLTYKPNSFNLS-IPVTVIGSGLGNHT-----ISCAPNHVSHQQFYDEC
SEQ ID NO:28      SALIGVDPVAGLSKQAQVEPKVLTFRPRSLD-PGMPALVVGTGLGP--KHVGGPPCAPAGVNHAEFYDEC
                  181                                                                    240

*   * *** * *                   *                      *   **
SEQ ID NO:19      KATKA-HFVAADYGHMDMLDDDLPGFVGF-MAGCMC-KNGQRKKSEMRSFVGGIVVAFLKYSLWGEKAEI
SEQ ID NO:20      QGPAW-HFVAKDYGHLDMLDDDDTKGIRGK-SSYCLC-KNGEERRP-MRRFVGGLVVSFLKAYLEGDDREL
SEQ ID NO:22      KNSSRAHFVATDYGHMDILDDNPSDVKSWALSKYFC-KNGNESRDPMRRCVSGIVVAFLKDFFYGDAEDF
SEQ ID NO:21      KENSS-HFVITKYGHMDMLNEFRLSPIAVTMSL-MCAQSFRP-KATMRRTLGGIMVAFLNAYFRDDGRQY
SEQ ID NO:28      -APPRYHVVLRDYGHMDMLDDDG----VPYVINNCMCMRNTKDTKDLARRAIGGAVVAFLRATLEDDDEDL
                  241                                                                    300

SEQ ID NO:19      RLIVKD-PSVSPAKLDPSPELEEAS-------GIFV
SEQ ID NO:20      -VKIKD-GCHE----DVPVEIQE-F------EVIM
SEQ ID NO:22      APIKLDSVEYIDASSMLTTHVKVRQILKD-PSF
SEQ ID NO:21      YAIIANR-SLAPTNL-FAEKKGFNFGFATTYAQL
SEQ ID NO:28      KVVLENRPGLSPAVLDPVG--------HDLA
                  361                             384
```

FIG. 2B ized. Three of different molecular

```
                        SEQUENCE LISTING

<160> NUMBER OF SEQ ID NOS: 30

<210> SEQ ID NO 1
<211> LENGTH: 987
<212> TYPE: DNA
<213> ORGANISM: Vitis sp.

<400> SEQUENCE: 1
cgagtggaga cttcaaacat cgcttcccct cccaagccat tgttgattgt tacaccaacc     60
attcaaggga catacccagt tctcttgttt cttcatggct tcgagctccg caacaccttc    120
tacactcagc tccttcaact catttcttcc catggattca ttgtggtggc tcctcagtta    180
tacggactat tacctccttc tggaattcaa gagatcaaat cagcagcagc agtcacaaat    240
tggctatcct caggccttca atctgtgctc ccagaaaatg tgaaaccaga cctactcaag    300
cttgctcttt caggccacag cagaggggga agacacagcat ttgctctggc actagggtat    360
gctgatacat ccctcaactt ctcagcccta ctaggactag accctgttgg tgggttgagt    420
aaatgttgcc aaacagttcc caaatcctaa acctatgttc ctcattcctt caatctagca    480
atcccagttt gcgtaatcgg cacggggttg ggcgatgagc caaggaactg cctaacatgt    540
ccatgtgccc cagatggagt gaaccatgta gagtttttca gtgagtgtaa acctccttgt    600
tcccactttg tgactactga atatggtcac ttggacatgt tagatgatca tctttcaggc    660
tgcattgggg cgatttcggg ttatatctgc aagagtggga agggtcctag ggaccccatg    720
aggagatgtg tgggtggcct ttttgttgca ttcttgaagg cttatttgga aggtcagact    780
ggagatttca aagccattgt tgatgaacct gatctggctc ctgtgaagct tgatcctgtt    840
gagttcatag aagcatgaaa tcatggattc tttgtaatgc tataaggagt gtgacagcag    900
attttttttt cggttcgtct ttgggaacaa agattcaaat aaacgaaact gtgttgtatt    960
gctaaaaaaa aaaaaaaaaa aaaaaaa                                         987

<210> SEQ ID NO 2
<211> LENGTH: 285
<212> TYPE: PRT
<213> ORGANISM: Vitis sp.

<400> SEQUENCE: 2

Arg Val Glu Thr Ser Asn Ile Ala Ser Pro Pro Lys Pro Leu Leu Ile
 1               5                  10                  15

Val Thr Pro Thr Ile Gln Gly Thr Tyr Pro Val Leu Leu Phe Leu His
             20                  25                  30

Gly Phe Glu Leu Arg Asn Thr Phe Tyr Thr Gln Leu Leu Gln Leu Ile
         35                  40                  45

Ser Ser His Gly Phe Ile Val Val Ala Pro Gln Leu Tyr Gly Leu Leu
     50                  55                  60

Pro Pro Ser Gly Ile Gln Glu Ile Lys Ser Ala Ala Ala Val Thr Asn
 65                  70                  75                  80

Trp Leu Ser Ser Gly Leu Gln Ser Val Leu Pro Glu Asn Val Lys Pro
                 85                  90                  95
```

```
Asp Leu Leu Lys Leu Ala Leu Ser Gly His Ser Arg Gly Gly Lys Thr
            100                 105                 110

Ala Phe Ala Leu Ala Leu Gly Tyr Ala Asp Thr Ser Leu Asn Phe Ser
        115                 120                 125

Ala Leu Leu Gly Leu Asp Pro Val Gly Gly Leu Ser Lys Cys Cys Gln
    130                 135                 140

Thr Val Pro Lys Ile Leu Thr Tyr Val Pro His Ser Phe Asn Leu Ala
145                 150                 155                 160

Ile Pro Val Cys Val Ile Gly Thr Gly Leu Gly Asp Glu Pro Arg Asn
                165                 170                 175

Cys Leu Thr Cys Pro Cys Ala Pro Asp Gly Val Asn His Val Glu Phe
            180                 185                 190

Phe Ser Glu Cys Lys Pro Pro Cys Ser His Phe Val Thr Thr Glu Tyr
        195                 200                 205

Gly His Leu Asp Met Leu Asp Asp His Leu Ser Gly Cys Ile Gly Ala
    210                 215                 220

Ile Ser Gly Tyr Ile Cys Lys Ser Gly Lys Gly Pro Arg Asp Pro Met
225                 230                 235                 240

Arg Arg Cys Val Gly Gly Leu Phe Val Ala Phe Leu Lys Ala Tyr Leu
                245                 250                 255

Glu Gly Gln Thr Gly Asp Phe Lys Ala Ile Val Asp Glu Pro Asp Leu
            260                 265                 270

Ala Pro Val Lys Leu Asp Pro Val Glu Phe Ile Glu Ala
        275                 280                 285

<210> SEQ ID NO 3
<211> LENGTH: 1216
<212> TYPE: DNA
<213> ORGANISM: Vitis sp.

<400> SEQUENCE: 3
cttctacatg ttccaccact gctgcaaatg tttttgagat tggaaagcac atcacagtgc      60
ttctaagagc tgaaccaggc acttgcacca ccaagtcatc tcttcctgtt cccccctccac    120 tgcaactctt gattgctacg ccctctgaag caggggagtt cccgctgctg ctcctccttc    180
atggttatct tctctataac tctttctact cccagctcat ccaacacata gcctctcatg    240
gtttcattgt tcttgctcct cagttataca ctgtggctgg accagattca agcgaagaga    300
tcaagtccgc agctgcttta acaaattggt tatccaaagg actccatgac ttacttcctc    360
cccatgttcg gccaaattta agcaaactag gacttgccgg ccatagtcgt ggaggcaaaa    420
ctgcttttgc tctagcactg agaaaagcat ccacttctct gaaattttca gccttgatag    480
gcatagaccc ggtggatgga atggacaaag ggaaacaaac ccctccaccg gtactcacct    540
atgttcctca ttcatttgat ctagacatgg cagtgatggt aattggttcg ggtttgggtg    600
aagtgaaaag gaaccctctg ttccctcctt gtgcccccaa gggcgtaaac catgaggact    660 tcttaaaga atgccgtgaa ccagcttgtt attttcttgc caaggactat ggccatcttg    720
acatgctaga cgatgagact aatgaattag agggaaagc tacacattgt ttgtgtaaaa    780
atgggaagtc tagagaaccc atgaggaggt tgttggagg cattgtgatt gcatttatga    840
aagcttattt ggaaggcgat aacagcagtc taatctccat tagagatggg catgctactg    900
caccagtgga gcttcaaaat gttgagtttc tcgtgtgaaa ttttaaatgt ttcgatttca    960
ataggtggca ttttctagt atgttatgaa tgcccaaagt tgttccccta attccaaggc   1020
aagatccaac tttattcgga tgcctgctta acaggcaata tcttaatgcc aacattagcc   1080
```

```
acaacttcta tcaaatcatt ggggtgttcc cctgatgcca gggcaaatag actctgtttg   1140
gatgcttggt tgactggaaa tatgataatg ccgtgtttgg tgaaaatttt tattagaaaa   1200
aaaaaaaaaa aaaaaa                                                   1216
```

<210> SEQ ID NO 4
<211> LENGTH: 311
<212> TYPE: PRT
<213> ORGANISM: Vitis sp.

<400> SEQUENCE: 4

```
Ser Thr Cys Ser Thr Thr Ala Ala Asn Val Phe Glu Ile Gly Lys His
 1               5                  10                  15

Ile Thr Val Leu Leu Arg Ala Glu Pro Gly Thr Cys Thr Thr Lys Ser
            20                  25                  30

Ser Leu Pro Val Pro Pro Leu Gln Leu Leu Ile Ala Thr Pro Ser
        35                  40                  45

Glu Ala Gly Glu Phe Pro Leu Leu Leu Leu His Gly Tyr Leu Leu
    50                  55                  60

Tyr Asn Ser Phe Tyr Ser Gln Leu Ile Gln His Ile Ala Ser His Gly
65                  70                  75                  80

Phe Ile Val Leu Ala Pro Gln Leu Tyr Thr Val Ala Gly Pro Asp Ser
                85                  90                  95

Ser Glu Glu Ile Lys Ser Ala Ala Leu Thr Asn Trp Leu Ser Lys
            100                 105                 110

Gly Leu His Asp Leu Leu Pro Pro His Val Arg Pro Asn Leu Ser Lys
        115                 120                 125

Leu Gly Leu Ala Gly His Ser Arg Gly Gly Lys Thr Ala Phe Ala Leu
    130                 135                 140

Ala Leu Arg Lys Ala Ser Thr Ser Leu Lys Phe Ser Ala Leu Ile Gly
145                 150                 155                 160

Ile Asp Pro Val Asp Gly Met Asp Lys Gly Lys Gln Thr Pro Pro Pro
                165                 170                 175

Val Leu Thr Tyr Val Pro His Ser Phe Asp Leu Asp Met Ala Val Met
            180                 185                 190

Val Ile Gly Ser Gly Leu Gly Glu Val Lys Arg Asn Pro Leu Phe Pro
        195                 200                 205

Pro Cys Ala Pro Lys Gly Val Asn His Glu Asp Phe Phe Lys Glu Cys
    210                 215                 220

Arg Glu Pro Ala Cys Tyr Phe Leu Ala Lys Asp Tyr Gly His Leu Asp
225                 230                 235                 240

Met Leu Asp Asp Glu Thr Asn Gly Ile Arg Gly Lys Ala Thr His Cys
                245                 250                 255

Leu Cys Lys Asn Gly Lys Ser Arg Glu Pro Met Arg Arg Phe Val Gly
            260                 265                 270

Gly Ile Val Ile Ala Phe Met Lys Ala Tyr Leu Glu Gly Asp Asn Ser
        275                 280                 285

Ser Leu Ile Ser Ile Arg Asp Gly His Ala Thr Ala Pro Val Glu Leu
    290                 295                 300

Gln Asn Val Glu Phe Leu Val
305                 310
```

<210> SEQ ID NO 5
<211> LENGTH: 1302
<212> TYPE: DNA

<213> ORGANISM: Zea mays

<400> SEQUENCE: 5

```
tcggccacga ttcccagtca tcaccaatta ttactgcctt tcgtccacaa ctactcatca      60
atccgatcga catgaacctc gcgtccgcgg tgcgagtgtt cttgtcctac tacctgctgg     120
tccaacggtg gatggggtcc gagcagggcg gaggcgtgtt cgatcagggg ggccatagcg     180
tcagcctcac ccgcctcgac gaagcaaggg cgccgccgag gtgcgccgtg cggtcgtccc     240
cgtccagcgc ggccagcctg ccgccgaagc cgctgctcgt cgccgcgccg cgcgagactg     300
gggagtaccc ggtgatcctg ttcctacacg gctacctcgc cgtcaactcc ttctactccc     360
agctgttcga gcacgtcgcc tcccatggct ttatcgtcgt cggacctcag ctgtacacca     420
tatctggggc cgacaccacc gaggagatca actcagcggc ggccgtcatc gactggctag     480
ccaccgggct gccgtcaact ctgccactcg gcgtccgcgc gaacctaacc aaggtgtcca     540
tctccggcca cagtcgcggc gggaaggtgg cgttcgcgct ggcgttgggc cacgccaagg     600
ccaagctcgc tgtccctctc gccgccgtcg tcgccgtgga cccggtggac ggcatgggcg     660
tgggcaagca gacaccgccg ccgatcctca cgggcaggca cggctcgctg cacgtgggtg     720
cccccgccat ggtcatcggc acggggctcg gcgagctgcc ccgcggctca ctgctcccgc     780
cgtgcgcgcc ccggggcgtc agtcacgcgg ccttctacga cgagctggac ggcgcggcgc     840
cagcgtgcca cctggtggtc agggactacg gcacacgga catgatggac gacgacacgc     900
cggggcgccag gggatgctc acgcgcacca tctgcaggag cggcgggggcc agggcgccca     960
tgcgccgctt cgtggccggc gccaccgtcg cgttcctcaa gaaatgggtg gctggggacg    1020
ccgcggcgat ggacagcatc acggcgcggc cggaccaggc ccccgtcgcg ctgtccgtgg    1080
tggagtttgg agatgagaaa gcgatagctt agctgctaga gaatatgtga tatctgcagg    1140
cactagccac tcaggcaggt tggtgacgac gttgaaattg cagatgaaat taactagagt    1200
ctagagatgg cacatggcag attggcagtg agtttcgaaa ctagctaatt tcctctctct    1260
tggcaaatca ataaaaaaaa aaaaaaaaaa aaaaaaaaaa aa                       1302
```

<210> SEQ ID NO 6
<211> LENGTH: 346
<212> TYPE: PRT
<213> ORGANISM: Zea mays

<400> SEQUENCE: 6

```
Met Asn Leu Ala Ser Ala Val Arg Val Phe Leu Ser Tyr Tyr Leu Leu
  1               5                  10                  15

Val Gln Arg Trp Met Gly Ser Glu Gln Gly Gly Val Phe Asp Gln
             20                  25                  30

Gly Gly His Ser Val Ser Leu Thr Arg Leu Asp Glu Ala Arg Ala Pro
         35                  40                  45

Pro Arg Cys Ala Val Arg Ser Ser Pro Ser Ala Ala Ser Leu Pro
     50                  55                  60

Pro Lys Pro Leu Leu Val Ala Ala Pro Arg Glu Thr Gly Glu Tyr Pro
 65                  70                  75                  80

Val Ile Leu Phe Leu His Gly Tyr Leu Ala Val Asn Ser Phe Tyr Ser
                 85                  90                  95

Gln Leu Phe Glu His Val Ala Ser His Gly Phe Ile Val Val Gly Pro
            100                 105                 110

Gln Leu Tyr Thr Ile Ser Gly Ala Asp Thr Thr Glu Glu Ile Asn Ser
        115                 120                 125
```

```
Ala Ala Ala Val Ile Asp Trp Leu Ala Thr Gly Leu Pro Ser Thr Leu
        130                 135                 140

Pro Leu Gly Val Arg Ala Asn Leu Thr Lys Val Ser Ile Ser Gly His
145                 150                 155                 160

Ser Arg Gly Gly Lys Val Ala Phe Ala Leu Ala Leu Gly His Ala Lys
                165                 170                 175

Ala Lys Leu Ala Val Pro Leu Ala Ala Val Val Ala Val Asp Pro Val
            180                 185                 190

Asp Gly Met Gly Val Gly Lys Gln Thr Pro Pro Ile Leu Thr Gly
        195                 200                 205

Arg His Gly Ser Leu His Val Gly Ala Pro Ala Met Val Ile Gly Thr
    210                 215                 220

Gly Leu Gly Glu Leu Pro Arg Gly Ser Leu Leu Pro Pro Cys Ala Pro
225                 230                 235                 240

Arg Gly Val Ser His Ala Ala Phe Tyr Asp Glu Leu Asp Gly Ala Ala
                245                 250                 255

Pro Ala Cys His Leu Val Val Arg Asp Tyr Gly His Thr Asp Met Met
            260                 265                 270

Asp Asp Asp Thr Pro Gly Ala Arg Gly Met Leu Thr Arg Thr Ile Cys
        275                 280                 285

Arg Ser Gly Gly Ala Arg Ala Pro Met Arg Arg Phe Val Ala Gly Ala
    290                 295                 300

Thr Val Ala Phe Leu Lys Lys Trp Val Ala Gly Asp Ala Ala Ala Met
305                 310                 315                 320

Asp Ser Ile Thr Ala Arg Pro Asp Gln Ala Pro Val Ala Leu Ser Val
                325                 330                 335

Val Glu Phe Gly Asp Glu Lys Ala Ile Ala
                340                 345

<210> SEQ ID NO 7
<211> LENGTH: 1174
<212> TYPE: DNA
<213> ORGANISM: Glycine max

<400> SEQUENCE: 7
ggaaagtgtt gatggcgcag agagctgaac caatattggt caccacagat gttttccaaa    60
tgggaaatat caaatggaag caattcaaca ttgatacatc caatgcttcc tcctcacctc   120
caaaaccatt gttaatcttt acaccaaccg tgcctggctc ataccctgta atattgttct   180
gccatggatt ttcccttcgc aatagctact actctgagct cctaggccac atagcttcac   240
atggattcat aattgttgct cctcagctgt gttggagtgt acggtctatg ttggaacctg   300
gtgatgaagt taaatttgca gggaaagttg tggattggct agccgaggag gggcttcaac   360
ctctgcttcc agagaatgtt gaagccaaat tggataaatt ggttttatca ggtcacagca   420
agggtggcaa aactgtattt gctgtggcac ttggttatgc taaaactaac ctcaagtttt   480
cagcactagt aggcatagac cctgtggctg gcccatgtaa atcttgcgaa acatttcctc   540
ctattctcac tggcatgtcc caatccttca atttgaacat accattgtt gtaattggca   600 ctgggctagg cccagagaag gctaattttt ttattccacc atgtgctcct gatgggtga   660 accataagga gtttttcaat aagtgcaaac ccccttgtgc acattttgtt gcaactgagt   720
atggtcacat ggacatgttg gatgatgtga cacctggctt aattgggtca atattgtcaa   780
attgtatatg caaggatggg aagggtccta gggacttgat gagaaggacc gtgggagggt   840
```

```
tggttgtggc cttcttaagg gcacagttga atggcctatg gaaggatttt aatgctgttt    900
tggcgaatcc taatcttgct cctactaaac tggatgatgt agtgtacgta cccgcatgaa    960
gtccatactc aatattaaag gctctttggt tcgatgctga attgctttca atgccaaagt   1020 ttctttcaa agaaatcaag tttctttcga tgatgtttgt ttttgtttcc ataaaaggct   1080
tgtaaatgga attttaaaat aatcttctat tgtttacatt ctctgtcgag tttttacgtg   1140
ggataatgtt tattcaaaaa aaaaaaaaaa aaaa                                1174
```

<210> SEQ ID NO 8
<211> LENGTH: 315
<212> TYPE: PRT
<213> ORGANISM: Glycine max

<400> SEQUENCE: 8

```
Met Ala Gln Arg Ala Glu Pro Ile Leu Val Thr Thr Asp Val Phe Gln
  1               5                  10                  15

Met Gly Asn Ile Lys Trp Lys Gln Phe Asn Ile Asp Thr Ser Asn Ala
                 20                  25                  30

Ser Ser Ser Pro Pro Lys Pro Leu Leu Ile Phe Thr Pro Thr Val Pro
             35                  40                  45

Gly Ser Tyr Pro Val Ile Leu Phe Cys His Gly Phe Ser Leu Arg Asn
         50                  55                  60

Ser Tyr Tyr Ser Glu Leu Leu Gly His Ile Ala Ser His Gly Phe Ile
 65                  70                  75                  80

Ile Val Ala Pro Gln Leu Cys Trp Ser Val Arg Ser Met Leu Glu Pro
                 85                  90                  95

Gly Asp Glu Val Lys Phe Ala Gly Lys Val Asp Trp Leu Ala Glu
            100                 105                 110

Glu Gly Leu Gln Pro Leu Leu Pro Glu Asn Val Glu Ala Lys Leu Asp
            115                 120                 125

Lys Leu Val Leu Ser Gly His Ser Lys Gly Gly Lys Thr Val Phe Ala
130                 135                 140

Val Ala Leu Gly Tyr Ala Lys Thr Asn Leu Lys Phe Ser Ala Leu Val
145                 150                 155                 160

Gly Ile Asp Pro Val Ala Gly Pro Cys Lys Ser Cys Glu Thr Phe Pro
                165                 170                 175

Pro Ile Leu Thr Gly Met Ser Gln Ser Phe Asn Leu Asn Ile Pro Ile
                180                 185                 190

Val Val Ile Gly Thr Gly Leu Gly Pro Glu Lys Ala Asn Phe Phe Ile
            195                 200                 205

Pro Pro Cys Ala Pro Asp Gly Val Asn His Lys Glu Phe Phe Asn Lys
210                 215                 220

Cys Lys Pro Pro Cys Ala His Phe Val Ala Thr Glu Tyr Gly His Met
225                 230                 235                 240

Asp Met Leu Asp Asp Val Thr Pro Gly Leu Ile Gly Ser Ile Leu Ser
                245                 250                 255

Asn Cys Ile Cys Lys Asp Gly Lys Gly Pro Arg Asp Leu Met Arg Arg
            260                 265                 270

Thr Val Gly Gly Leu Val Val Ala Phe Leu Arg Ala Gln Leu Asn Gly
            275                 280                 285

Leu Trp Lys Asp Phe Asn Ala Val Leu Ala Asn Pro Asn Leu Ala Pro
290                 295                 300

Thr Lys Leu Asp Asp Val Val Tyr Val Pro Ala
305                 310                 315
```

<210> SEQ ID NO 9
<211> LENGTH: 1104
<212> TYPE: DNA
<213> ORGANISM: Glycine max

<400> SEQUENCE: 9

```
gcacgagtgt gagaagagtg gtgtgatggc gcagagagct caaccagtat tggccacaga      60
tgttttccaa atgggaaaca tccaatggaa gcaattcaat gttgatacat ccagtgcttc     120
cttctcacct ccaaaaccat tgctaatttt tacaccaact gttcctggcg catacccctgt    180
aatattgttc gtccatggct ttttcattcg caatttctac tactcaaagc tcctagccca    240
catagtctca catggattca taatcgttgc tcctcaactg ttttccaatg ggcttcctat    300
gtatggaccc actgaagtgg aatatgcagg aaaagttgcg gattggatag ctgaggagct    360
tcaacatttg cttccagaga acgttgaagc caatttggac aaactggttc tatcaggtca    420
cagtagggt gggaaaactg tatttgctgt ggctcttggt catgcaaaaa ctaatctcaa     480
gttttcagca cttgtaggca tagaccctgt ggctggcaca tctaaatatt gtagaacacg    540
tcctcatatt ctcactggca agccacggtc ctttgatttg aaaatgccag ttgaagtaat    600
tggcactgga ttgggcccag agaagcttaa ttgttgtact ccaccgtgtg ctcctgatgg    660
ggtgaactat aaggagttct tcaacgagtg caaacccct tgtgctaaat tgttgtagc     720
aaagtatggt cacatggaca tgttgaatga tgacacacca gggctaattg ggacattggt    780
gtcaaagtgt atgtgtaaga atgggacgac gggtcctagg gacttgatga aaggaccac    840
tggaggttg gttgtgtcct tcttgagggc acaattgaat gacctatgga aggattttga    900
tgctatttta aaggacccta atcttgctcc cactgaagtc gatggtgtag actacatacc    960
agcatgaatt gatcaacact caacgttctt ttgcgctttt atttccctga aaggcctata   1020
aatgtctttc gaaataatcg tctatggtta tttatgtatt ctcgctatcc tgtcatagta   1080
taagaaaaaa aaaaaaaaa aaaa                                            1104
```

<210> SEQ ID NO 10
<211> LENGTH: 313
<212> TYPE: PRT
<213> ORGANISM: Glycine max

<400> SEQUENCE: 10

```
Met Ala Gln Arg Ala Gln Pro Val Leu Ala Thr Asp Val Phe Gln Met
 1               5                  10                  15

Gly Asn Ile Gln Trp Lys Gln Phe Asn Val Asp Thr Ser Ser Ala Ser
            20                  25                  30

Phe Ser Pro Pro Lys Pro Leu Leu Ile Phe Thr Pro Thr Val Pro Gly
        35                  40                  45

Ala Tyr Pro Val Ile Leu Phe Val His Gly Phe Phe Ile Arg Asn Phe
    50                  55                  60

Tyr Tyr Ser Lys Leu Leu Ala His Ile Val Ser His Gly Phe Ile Ile
65                  70                  75                  80

Val Ala Pro Gln Leu Phe Ser Asn Gly Leu Pro Met Tyr Gly Pro Thr
                85                  90                  95

Glu Val Glu Tyr Ala Gly Lys Val Ala Asp Trp Ile Ala Glu Glu Leu
            100                 105                 110

Gln His Leu Leu Pro Glu Asn Val Glu Ala Asn Leu Asp Lys Leu Val
        115                 120                 125
```

-continued

| | | | | | | | | | | | | |
|---|---|---|---|---|---|---|---|---|---|---|---|---|
|Leu|Ser|Gly|His|Ser|Arg|Gly|Gly|Lys|Thr|Val|Phe|Ala Val Ala Leu|
| |130| | | |135| | | |140| | | |

Gly His Ala Lys Thr Asn Leu Lys Phe Ser Ala Leu Val Gly Ile Asp
145                 150                 155                 160

Pro Val Ala Gly Thr Ser Lys Tyr Cys Arg Thr Arg Pro His Ile Leu
                165                 170                 175

Thr Gly Lys Pro Arg Ser Phe Asp Leu Lys Met Pro Val Glu Val Ile
            180                 185                 190

Gly Thr Gly Leu Gly Pro Glu Lys Leu Asn Cys Cys Thr Pro Pro Cys
        195                 200                 205

Ala Pro Asp Gly Val Asn Tyr Lys Glu Phe Phe Asn Glu Cys Lys Pro
210                 215                 220

Pro Cys Ala Lys Phe Val Val Ala Lys Tyr Gly His Met Asp Met Leu
225                 230                 235                 240

Asn Asp Asp Thr Pro Gly Leu Ile Gly Thr Leu Val Ser Lys Cys Met
                245                 250                 255

Cys Lys Asn Gly Thr Thr Gly Pro Arg Asp Leu Met Arg Arg Thr Thr
            260                 265                 270

Gly Gly Leu Val Val Ser Phe Leu Arg Ala Gln Leu Asn Asp Leu Trp
        275                 280                 285

Lys Asp Phe Asp Ala Ile Leu Lys Asp Pro Asn Leu Ala Pro Thr Glu
290                 295                 300

Val Asp Gly Val Asp Tyr Ile Pro Ala
305                 310

<210> SEQ ID NO 11
<211> LENGTH: 1125
<212> TYPE: DNA
<213> ORGANISM: Glycine max

<400> SEQUENCE: 11

| | | |
|---|---|---|
|tagaacatag aagcaaagtg tttggtgtga agagagagat aatggcgcag agagctcaac|60|
|cagcgttggc caccacggat gttttttcaga agggagatat tcattggaag caattcaatg|120|
|ttgaaacatc cactgcttct tcctcacctc caaaaccatt gcttattttt acaccaaccg|180|
|tgcctggctt atacccgtta atattgtttt gccatggctt ttgtattcgc actagctact|240|
|actctaagct cctagcccac atagtttcac atggattcat acttgttgct cctcagctgt|300|
|tttccattgg ggtgcctatg tttgaccag aagaagttaa gtgtgaagga agagttgtgg|360|
|attggctaga taacgggctt caaccattgc ttcccgagag cgttgaagcc aaactggaga|420|
|aactggttct agtaggtcac agcaagggtg gaaaaacagc atttgctgtg cacttggtt|480|
|actgtaaaac aaagctcaag ttttcagcac tcataggcat agatcctgtg ctggcgtat|540|
|caaagtgtaa gccttgtcga tcacttcctg atatcctcac aggtgtgcca cggtccttta|600|
|atctgaacat acctgttgct gtaattggaa ctgggttggg cccagagaag gctaattctc|660|
|tttttccacc atgtgctcca atggggtga accataaaga gttttctct gagtgcaaac|720|
|cacctagtgc atattttgtt gcaacggatt atggtcacat ggacatgttg gatgatgaaa|780|
|caccagggt aattgggaca atgatgtcaa agtgtatgtg caagaatggg aagaagggtc|840|
|ctagggactt gatgagaagg actgtgggag gttggttgt ggccttcttg agagcacagt|900|
|tgaatgagca gtggaaggat tttgatgcta ttttagcgag tcctaatcta gctcccgcca|960|
|aacttgatga tgtgcgatac ttaccaacat gaagtcatca cacaaacatt catttatgca|1020|
|gttttattc tatttctatg aaaggcctat aatgtctttc aaatttgtct atataatgat|1080| gtgattcaca ttgcactttt caaaaaaaaa aaaaaaaaac tcgag                    1125

<210> SEQ ID NO 12
<211> LENGTH: 316
<212> TYPE: PRT
<213> ORGANISM: Glycine max

<400> SEQUENCE: 12

Met Ala Gln Arg Ala Gln Pro Ala Leu Ala Thr Thr Asp Val Phe Gln
1               5                   10                  15

Lys Gly Asp Ile His Trp Lys Gln Phe Asn Val Glu Thr Ser Thr Ala
            20                  25                  30

Ser Ser Ser Pro Pro Lys Pro Leu Leu Ile Phe Thr Pro Thr Val Pro
        35                  40                  45

Gly Leu Tyr Pro Val Ile Leu Phe Cys His Gly Phe Cys Ile Arg Thr
    50                  55                  60

Ser Tyr Tyr Ser Lys Leu Leu Ala His Ile Val Ser His Gly Phe Ile
65                  70                  75                  80

Leu Val Ala Pro Gln Leu Phe Ser Ile Gly Val Pro Met Phe Gly Pro
                85                  90                  95

Glu Glu Val Lys Cys Glu Gly Arg Val Val Asp Trp Leu Asp Asn Gly
            100                 105                 110

Leu Gln Pro Leu Leu Pro Glu Ser Val Glu Ala Lys Leu Glu Lys Leu
        115                 120                 125

Val Leu Val Gly His Ser Lys Gly Gly Lys Thr Ala Phe Ala Val Ala
    130                 135                 140

Leu Gly Tyr Cys Lys Thr Lys Leu Lys Phe Ser Ala Leu Ile Gly Ile
145                 150                 155                 160

Asp Pro Val Ala Gly Val Ser Lys Cys Lys Pro Cys Arg Ser Leu Pro
                165                 170                 175

Asp Ile Leu Thr Gly Val Pro Arg Ser Phe Asn Leu Asn Ile Pro Val
            180                 185                 190

Ala Val Ile Gly Thr Gly Leu Gly Pro Glu Lys Ala Asn Ser Leu Phe
        195                 200                 205

Pro Pro Cys Ala Pro Asn Gly Val Asn His Lys Glu Phe Phe Ser Glu
    210                 215                 220

Cys Lys Pro Pro Ser Ala Tyr Phe Val Ala Thr Asp Tyr Gly His Met
225                 230                 235                 240

Asp Met Leu Asp Asp Glu Thr Pro Gly Val Ile Gly Thr Met Met Ser
                245                 250                 255

Lys Cys Met Cys Lys Asn Gly Lys Lys Gly Pro Arg Asp Leu Met Arg
            260                 265                 270

Arg Thr Val Gly Gly Leu Val Val Ala Phe Leu Arg Ala Gln Leu Asn
        275                 280                 285

Glu Gln Trp Lys Asp Phe Asp Ala Ile Leu Ala Ser Pro Asn Leu Ala
    290                 295                 300

Pro Ala Lys Leu Asp Asp Val Arg Tyr Leu Pro Thr
305                 310                 315

<210> SEQ ID NO 13
<211> LENGTH: 1444
<212> TYPE: DNA
<213> ORGANISM: Gesneriana

<400> SEQUENCE: 13

-continued

| | |
|---|---|
| gcacgaggca aatagacat tgtttttttt cttttttgaa aattgccaac cctgggaggt | 60 |
| gttgacgggg ttaagtccag actagacatt gttatcatgg catcttctcc ttgctccgtt | 120 |
| tttgtgcctg ggaagtacac ggtccaactg aaaagcgtcg aggccggcac taagaaggcc | 180 |
| aggcatgtta gctctgtctc cgcaccacct cggaagccac cactgatcgc aactccattt | 240 |
| gaggaaggcg agtacccaac gcttctactc cttcatggat tcatgcttca caacactttc | 300 |
| tactctgagc ttatccagca catcgcatcc catggcttta ttgttgttgt acctcagtta | 360 |
| tatcttgtag ctacatgtga tagtacgaat ggcatcaagt ctgctgcaaa acaacagat | 420 |
| tggttgaagg atggactgca agatgttctc ccaacaaaag tcagaccaga cctaaagaaa | 480 |
| ctcggactga gcggacatag ccgtggcggc aaagatgcat ttgctcttgc actaggatat | 540 |
| gcgaagacta cattaagctt ctcagcgctg atcgggatcg atcctgttga cggagtacga | 600 |
| aagggacacc aaaccaatcc tcctgtactg aattatatcc ctcactcttt ggaactcaag | 660 |
| atgccgtcat tagttatcgg aacaggttta ggtgaattga gaggaacct atttgcctgt | 720 |
| gcccctaagg gagtaaatca ccaagatttt tacgatgagt gttcttcccc gtcttgccat | 780 |
| tttgttgcta aggactatgg tcacatggac atgctagatg atcatactga cggacctaga | 840 |
| ggtattgtgt catactgcat gtgtcgaaat ggagaatcaa gaacacccat gcgactgttt | 900 |
| gtaggtggga tcgtggttgc ttttctgaaa gcctgcttac aaggtgataa acaggatttg | 960 |
| cgagctctga aggataaccc cgagatttca aatattaact tatcaattgt cgacttctat | 1020 |
| gatcctgatg ggacattgac gaaatatttt gatggtggtt caatttccac accacattac | 1080 |
| gcagtccaag aaagccatca acaatgatat ttcaatgcag agacgcacaa ctaatgattg | 1140 |
| cctgcaaata tgaagttccg tattagattc atataatgaa ctaggatatc tctttcatct | 1200 |
| aaatagtcca tgtattttat ttcatgcaga gtatgtttaa tctatgtaat aagagacact | 1260 |
| actagtatct atcgtcagca gcatggcaat ttaaaactct gtaaactctc agaattatga | 1320 |
| ttgtatcttg gcggttagcc ttgacaaaaa agagaggcac tattagcaag tggaaaaaaa | 1380 |
| aaaaaaaaaa aaaaaaaaaa aaaaaaaaaa aaaaaaaaaa aaaaaaaaaa aaaaaaaaaa | 1440 |
| aaaa | 1444 |

<210> SEQ ID NO 14
<211> LENGTH: 336
<212> TYPE: PRT
<213> ORGANISM: Gesneriana

<400> SEQUENCE: 14

```
Met Ala Ser Ser Pro Cys Ser Val Phe Val Pro Gly Lys Tyr Thr Val
  1               5                  10                  15

Gln Leu Lys Ser Val Glu Ala Gly Thr Lys Lys Ala Arg His Val Ser
             20                  25                  30

Ser Val Ser Ala Pro Pro Arg Lys Pro Pro Leu Ile Ala Thr Pro Phe
         35                  40                  45

Glu Glu Gly Glu Tyr Pro Thr Leu Leu Leu Leu His Gly Phe Met Leu
     50                  55                  60

His Asn Thr Phe Tyr Ser Glu Leu Ile Gln His Ile Ala Ser His Gly
 65                  70                  75                  80

Phe Ile Val Val Val Pro Gln Leu Tyr Leu Val Ala Thr Cys Asp Ser
                 85                  90                  95

Thr Asn Gly Ile Lys Ser Ala Ala Lys Thr Thr Asp Trp Leu Lys Asp
            100                 105                 110
```

| | | | | | | | | | | | |
|---|---|---|---|---|---|---|---|---|---|---|---|
|Gly|Leu|Gln|Asp|Val|Leu|Pro|Thr|Lys|Val|Arg|Pro|Asp|Leu|Lys|Lys|
| |115| | | |120| | | |125| | | | | | |

Leu Gly Leu Ser Gly His Ser Arg Gly Gly Lys Asp Ala Phe Ala Leu
    130             135             140

Ala Leu Gly Tyr Ala Lys Thr Thr Leu Ser Phe Ser Ala Leu Ile Gly
145             150                 155                 160

Ile Asp Pro Val Asp Gly Val Arg Lys Gly His Gln Thr Asn Pro Pro
            165                 170                 175

Val Leu Asn Tyr Ile Pro His Ser Leu Glu Leu Lys Met Pro Ser Leu
        180                 185                 190

Val Ile Gly Thr Gly Leu Gly Glu Leu Lys Arg Asn Leu Phe Ala Cys
        195                 200                 205

Ala Pro Lys Gly Val Asn His Gln Asp Phe Tyr Asp Glu Cys Ser Ser
    210                 215                 220

Pro Ser Cys His Phe Val Ala Lys Asp Tyr Gly His Met Asp Met Leu
225                 230                 235                 240

Asp Asp His Thr Asp Gly Pro Arg Gly Ile Val Ser Tyr Cys Met Cys
            245                 250                 255

Arg Asn Gly Glu Ser Arg Thr Pro Met Arg Leu Phe Val Gly Gly Ile
            260                 265                 270

Val Val Ala Phe Leu Lys Ala Cys Leu Gln Gly Asp Lys Gln Asp Leu
        275                 280                 285

Arg Ala Leu Lys Asp Asn Pro Glu Ile Ser Asn Ile Asn Leu Ser Ile
    290                 295                 300

Val Asp Phe Tyr Asp Pro Asp Gly Thr Leu Thr Lys Tyr Phe Asp Gly
305                 310                 315                 320

Gly Ser Ile Ser Thr Pro His Tyr Ala Val Gln Glu Ser His Gln Gln
            325                 330                 335

<210> SEQ ID NO 15
<211> LENGTH: 916
<212> TYPE: DNA
<213> ORGANISM: Triticum aestivum

<400> SEQUENCE: 15

```
ccacgagtcg agcctgacct gtccaagctg gccctagccg gccatagccg aggcggccag      60
acggccttcg ccgtcgccct gggactaggg gacgccaaga ccaagctgga gctcaagttc     120
tccgccctca tcggcgtcga ccccgtggcc ggggtttcca gagcccaaca gttggagccc     180
aaggtgctca cttttgaacc tgactgtctc gacgtgggga tgccggtgct ggtcatgggg     240
actgggctgg gtcccaagca catcggcgga tttccatgcg ccccgtgggg cgtgaaccac     300
gccgaattct acaaggagtg cgcgccgcct cgctaccacc tcgtggtcaa ggactacggg     360
catctcgaca tgctggatga caatgtgccc tatatcatca caactgcat gtgcatgagg      420
aaccaacacg acaccaaaga tcttgctagg aggaccatgg aggagccat ggttgccttc      480
ctcagggcta aattgcgaat cgatgttcgt gatctcatcg ccatatatca taatcctgag     540
atcgcgccag ccgtcctgga ccaagttgat gagtttcttc cttgcttcgt tggacggcca     600
aatccgtcgt ctgtgtgaga gttatattac gtgcctatgc ctatctatta ctcctaaata     660
aggtgtgttg gtgcatggcc ttgtcatggc tcatgactac tatagcacgt ccagtcttcc     720
taattactaa ataataagca ctaatgtcat gtgtgcatgt atctatgtag aatatatatg     780
tgttgtgtgc tatttatcaa tccttaaatg atgttcatgt accctcaaaa caaaatgtat     840
ttattttgtt gtgaagtttc ctactttatt ttctcatact ataacttgga actaaaaaaa     900
```
aaaaaaaaaa aaaaaa                                                           916

<210> SEQ ID NO 16
<211> LENGTH: 205
<212> TYPE: PRT
<213> ORGANISM: Triticum aestivum

<400> SEQUENCE: 16

Pro Arg Val Glu Pro Asp Leu Ser Lys Leu Ala Leu Ala Gly His Ser
 1               5                  10                  15

Arg Gly Gly Gln Thr Ala Phe Ala Val Ala Leu Gly Leu Gly Asp Ala
            20                  25                  30

Lys Thr Lys Leu Glu Leu Lys Phe Ser Ala Leu Ile Gly Val Asp Pro
        35                  40                  45

Val Ala Gly Val Ser Arg Ala Gln Gln Leu Glu Pro Lys Val Leu Thr
    50                  55                  60

Phe Glu Pro Asp Cys Leu Asp Val Gly Met Pro Val Leu Val Met Gly
65                  70                  75                  80

Thr Gly Leu Gly Pro Lys His Ile Gly Gly Phe Pro Cys Ala Pro Val
                85                  90                  95

Gly Val Asn His Ala Glu Phe Tyr Lys Glu Cys Ala Pro Pro Arg Tyr
            100                 105                 110

His Leu Val Val Lys Asp Tyr Gly His Leu Asp Met Leu Asp Asp Asn
        115                 120                 125

Val Pro Tyr Ile Ile Asn Asn Cys Met Cys Met Arg Asn Gln His Asp
    130                 135                 140

Thr Lys Asp Leu Ala Arg Arg Thr Met Gly Gly Ala Met Val Ala Phe
145                 150                 155                 160

Leu Arg Ala Lys Leu Arg Ile Asp Val Arg Asp Leu Ile Ala Ile Tyr
                165                 170                 175

His Asn Pro Glu Ile Ala Pro Ala Val Leu Asp Gln Val Asp Glu Phe
            180                 185                 190

Leu Pro Cys Phe Val Gly Arg Pro Asn Pro Ser Ser Val
        195                 200                 205

<210> SEQ ID NO 17
<211> LENGTH: 1242
<212> TYPE: DNA
<213> ORGANISM: Triticum aestivum

<400> SEQUENCE: 17
gcacgaggtt aagacagaga gttggtgccc tgagcttgag tgagagatgg cagcagcagc    60
acccgcagag acgatgaaca agtccgccgc cggcgccgag gttcccgagg cgttcacatc   120
ggtgttccag ccggggaagc ttgcggtcga ggcgattcag gtggatgaga atgcggcgcc   180
gacaccaccg atcccggtgc tgatcgtcgc acccaaggat gcaggaacct accccgtggc   240
catgctcttg cacggcttct cctccataa ccacttctac gaacaccttc tccggcacgt   300
cgcatcccac ggcttcatca ttgtcgcgcc ccagttcagc atcagtatca taccttcggg   360
tgacgcagag gacatcgccg cggcagccaa ggtggcagac tggctccccg acggcctccc   420
gtccgtgctg cccaaaggcg tcgagccgga gctctcgaag ctcgccttgg ccggccacag   480
ccgaggaggc cacacggctt tctccctggc cttggggcac gccaagaccc agctaacctt   540
ctccgcgctc atcggactcg accccgtcgc cggcacgggg aagtcctccc agctccagcc   600
caagatcctc acctacgagc cgtcctcctt cggcatggcg atgccggtgc tggtcatcgg   660

-continued

```
caccgggctc ggcgaggaga agaagaacat attcttccct ccctgcgcac ccaaggacgt    720
gaaccacgcc gagttctacc gcgagtgcag gccgccctgc tactactttg tgaccaagga    780
ctacgggcat ctggacatgc tggacgacga cgcccccaag ttcatcacct gcgtctgcaa    840
ggatgggaac gggtgcaagg gcaagatgcg gaggtgcgtt gctgggatca tggtggcatt    900
tcttaatgct gccttgggtg agaaagatgc agatcttgag ccatactga gagacccggc     960 ggttgcaccc accacgcttg atccggttga gcaccgcgtg gcgtgaagca gcagctggct   1020
catgccaaaa gttaaccagc cgcaggttgg tccactaaat aaagtacaga tgtactgtac   1080
ctctgagcaa tttgcttcac ttgttcatgc aagctaaaac tgctgctgct ttacttcttg   1140
ctcctgcgag cctgcaatgg tacttctgct ctgtttccag atgtatacta ctcctgtgag   1200
tataatcttg tttttcgtgt ctaaaaaaaa aaaaaaaaa aa                       1242
```

<210> SEQ ID NO 18
<211> LENGTH: 319
<212> TYPE: PRT
<213> ORGANISM: Triticum aestivum

<400> SEQUENCE: 18

```
Met Ala Ala Ala Pro Ala Glu Thr Met Asn Lys Ser Ala Ala Gly
  1               5                  10                  15

Ala Glu Val Pro Glu Ala Phe Thr Ser Val Phe Gln Pro Gly Lys Leu
                 20                  25                  30

Ala Val Glu Ala Ile Gln Val Asp Glu Asn Ala Ala Pro Thr Pro Pro
             35                  40                  45

Ile Pro Val Leu Ile Val Ala Pro Lys Asp Ala Gly Thr Tyr Pro Val
         50                  55                  60

Ala Met Leu Leu His Gly Phe Phe Leu His Asn His Phe Tyr Glu His
     65                  70                  75                  80

Leu Leu Arg His Val Ala Ser His Gly Phe Ile Val Ala Pro Gln
                 85                  90                  95

Phe Ser Ile Ser Ile Pro Ser Gly Asp Ala Glu Asp Ile Ala Ala
            100                 105                 110

Ala Ala Lys Val Ala Asp Trp Leu Pro Asp Gly Leu Pro Ser Val Leu
        115                 120                 125

Pro Lys Gly Val Glu Pro Glu Leu Ser Lys Leu Ala Leu Ala Gly His
    130                 135                 140

Ser Arg Gly Gly His Thr Ala Phe Ser Leu Ala Leu Gly His Ala Lys
145                 150                 155                 160

Thr Gln Leu Thr Phe Ser Ala Leu Ile Gly Leu Asp Pro Val Ala Gly
                165                 170                 175

Thr Gly Lys Ser Ser Gln Leu Gln Pro Lys Ile Leu Thr Tyr Glu Pro
            180                 185                 190

Ser Ser Phe Gly Met Ala Met Pro Val Leu Val Ile Gly Thr Gly Leu
        195                 200                 205

Gly Glu Glu Lys Lys Asn Ile Phe Phe Pro Cys Ala Pro Lys Asp
    210                 215                 220

Val Asn His Ala Glu Phe Tyr Arg Glu Cys Arg Pro Pro Cys Tyr Tyr
225                 230                 235                 240

Phe Val Thr Lys Asp Tyr Gly His Leu Asp Met Leu Asp Asp Asp Ala
                245                 250                 255

Pro Lys Phe Ile Thr Cys Val Cys Lys Asp Gly Asn Gly Cys Lys Gly
            260                 265                 270
```

```
Lys Met Arg Arg Cys Val Ala Gly Ile Met Val Ala Phe Leu Asn Ala
            275                 280                 285

Ala Leu Gly Glu Lys Asp Ala Asp Leu Glu Ala Ile Leu Arg Asp Pro
        290                 295                 300

Ala Val Ala Pro Thr Thr Leu Asp Pro Val Glu His Arg Val Ala
305                 310                 315
```

<210> SEQ ID NO 19
<211> LENGTH: 324
<212> TYPE: PRT
<213> ORGANISM: Arabidopsis thaliana

<400> SEQUENCE: 19

```
Met Ala Ala Ile Glu Asp Ser Pro Thr Phe Ser Ser Val Val Thr Pro
1               5                   10                  15

Ala Ala Phe Glu Ile Gly Ser Leu Pro Thr Thr Glu Ile Pro Val Asp
            20                  25                  30

Pro Val Glu Asn Asp Ser Thr Ala Pro Pro Lys Pro Val Arg Ile Thr
        35                  40                  45

Cys Pro Thr Val Ala Gly Thr Tyr Pro Val Leu Phe Phe His Gly
    50                  55                  60

Phe Tyr Leu Arg Asn Tyr Phe Tyr Ser Asp Val Leu Asn His Ile Ala
65                  70                  75                  80

Ser His Gly Tyr Ile Leu Val Ala Pro Gln Leu Cys Lys Leu Leu Pro
                85                  90                  95

Pro Gly Gly Gln Val Glu Val Asp Asp Ala Gly Ser Val Ile Asn Trp
            100                 105                 110

Ala Ser Glu Asn Leu Lys Ala His Leu Pro Thr Ser Val Asn Ala Asn
        115                 120                 125

Gly Lys Tyr Thr Ser Leu Val Gly His Ser Arg Gly Gly Lys Thr Ala
    130                 135                 140

Phe Ala Val Ala Leu Gly His Ala Ala Thr Leu Asp Pro Ser Ile Thr
145                 150                 155                 160

Phe Ser Ala Leu Ile Gly Ile Asp Pro Val Ala Gly Thr Asn Lys Tyr
                165                 170                 175

Ile Arg Thr Asp Pro His Ile Leu Thr Tyr Lys Pro Glu Ser Phe Glu
            180                 185                 190

Leu Asp Ile Pro Val Ala Val Val Gly Thr Gly Leu Gly Pro Lys Trp
        195                 200                 205

Asn Asn Val Met Pro Pro Cys Ala Pro Thr Asp Leu Asn His Glu Glu
    210                 215                 220

Phe Tyr Lys Glu Cys Lys Ala Thr Lys Ala His Phe Val Ala Ala Asp
225                 230                 235                 240

Tyr Gly His Met Asp Met Leu Asp Asp Asp Leu Pro Gly Phe Val Gly
                245                 250                 255

Phe Met Ala Gly Cys Met Cys Lys Asn Gly Gln Arg Lys Lys Ser Glu
            260                 265                 270

Met Arg Ser Phe Val Gly Gly Ile Val Val Ala Phe Leu Lys Tyr Ser
        275                 280                 285

Leu Trp Gly Glu Lys Ala Glu Ile Arg Leu Ile Val Lys Asp Pro Ser
    290                 295                 300

Val Ser Pro Ala Lys Leu Asp Pro Ser Pro Glu Leu Glu Glu Ala Ser
305                 310                 315                 320

Gly Ile Phe Val
```

```
<210> SEQ ID NO 20
<211> LENGTH: 318
<212> TYPE: PRT
<213> ORGANISM: Arabidopsis thaliana

<400> SEQUENCE: 20

Met Ser Ser Ser Ser Arg Asn Ala Phe Glu Asp Gly Lys Tyr Lys
 1               5                  10                  15

Ser Asn Leu Leu Thr Leu Asp Ser Ser Arg Cys Cys Lys Ile Thr
                20                  25                  30

Pro Ser Ser Arg Ala Ser Pro Ser Pro Lys Gln Leu Leu Val Ala
                35                  40                  45

Thr Pro Val Glu Glu Gly Asp Tyr Pro Val Val Met Leu Leu His Gly
            50                  55                  60

Tyr Leu Leu Tyr Asn Ser Phe Tyr Ser Gln Leu Met Leu His Val Ser
65                  70                  75                  80

Ser His Gly Phe Ile Leu Ile Ala Pro Gln Leu Tyr Ser Ile Ala Gly
                    85                  90                  95

Pro Asp Thr Met Asp Glu Ile Lys Ser Thr Ala Glu Ile Met Asp Trp
                100                 105                 110

Leu Ser Val Gly Leu Asn His Phe Leu Pro Ala Gln Val Thr Pro Asn
            115                 120                 125

Leu Ser Lys Phe Ala Leu Ser Gly His Ser Arg Gly Gly Lys Thr Ala
        130                 135                 140

Phe Ala Val Ala Leu Lys Lys Phe Gly Tyr Ser Ser Asn Leu Lys Ile
145                 150                 155                 160

Ser Thr Leu Ile Gly Ile Asp Pro Val Asp Gly Thr Gly Lys Gly Lys
                165                 170                 175

Gln Thr Pro Pro Pro Val Leu Ala Tyr Leu Pro Asn Ser Phe Asp Leu
            180                 185                 190

Asp Lys Thr Pro Ile Leu Val Ile Gly Ser Gly Leu Gly Glu Thr Ala
        195                 200                 205

Arg Asn Pro Leu Phe Pro Pro Cys Ala Pro Pro Gly Val Asn His Arg
    210                 215                 220

Glu Phe Arg Glu Cys Gln Gly Pro Ala Trp His Phe Val Ala Lys
225                 230                 235                 240

Asp Tyr Gly His Leu Asp Met Leu Asp Asp Thr Lys Gly Ile Arg
                245                 250                 255

Gly Lys Ser Ser Tyr Cys Leu Cys Lys Asn Gly Glu Glu Arg Arg Pro
            260                 265                 270

Met Arg Arg Phe Val Gly Gly Leu Val Val Ser Phe Leu Lys Ala Tyr
        275                 280                 285

Leu Glu Gly Asp Asp Arg Glu Leu Val Lys Ile Lys Asp Gly Cys His
    290                 295                 300

Glu Asp Val Pro Val Glu Ile Gln Glu Phe Glu Val Ile Met
305                 310                 315

<210> SEQ ID NO 21
<211> LENGTH: 347
<212> TYPE: PRT
<213> ORGANISM: Chenopodium album

<400> SEQUENCE: 21

Met Ala Lys Leu Leu Leu Leu Ile Phe Gly Val Phe Ile Phe Val Asn
 1               5                  10                  15
```

```
Ser Gln Ala Gln Thr Phe Pro Thr Ile Leu Glu Lys His Asn Ser Glu
            20                  25                  30

Lys Ile Thr Asp Val Phe His Lys Gly Asn Phe Gln Val Thr Asn Asn
        35                  40                  45

Pro Ile Arg Val Lys Arg Tyr Glu Phe Ser Ala Pro Glu Pro Leu Ile
    50                  55                  60

Ile Ile Ser Pro Lys Glu Ala Gly Val Tyr Pro Val Leu Leu Phe Ile
65                  70                  75                  80

His Gly Thr Met Leu Ser Asn Glu Asp Tyr Ser Leu Phe Phe Asn Tyr
                85                  90                  95

Ile Ala Ser His Gly Phe Ile Val Val Ala Pro Lys Leu Phe Arg Leu
            100                 105                 110

Phe Pro Pro Lys Leu Pro Ser Gln Gln Asp Glu Ile Asp Met Ala Ala
            115                 120                 125

Ser Val Ala Asn Trp Met Pro Leu Tyr Leu Gln Val Val Leu Gln Arg
130                 135                 140

Tyr Val Thr Gly Val Glu Gly Asp Leu Glu Lys Leu Ala Ile Ser Gly
145                 150                 155                 160

His Ser Arg Gly Gly Lys Ser Ala Phe Ala Leu Ala Leu Gly Phe Ser
                165                 170                 175

Asn Ile Lys Leu Asp Val Thr Phe Ser Ala Leu Ile Gly Val Asp Pro
            180                 185                 190

Val Ala Gly Arg Ser Val Asp Asp Arg Thr Leu Pro His Val Leu Thr
        195                 200                 205

Tyr Lys Pro Asn Ser Phe Asn Leu Ser Ile Pro Val Thr Val Ile Gly
    210                 215                 220

Ser Gly Leu Gly Asn His Thr Ile Ser Cys Ala Pro Asn His Val Ser
225                 230                 235                 240

His Gln Gln Phe Tyr Asp Glu Cys Lys Glu Asn Ser Ser His Phe Val
                245                 250                 255

Ile Thr Lys Tyr Gly His Met Asp Met Leu Asn Glu Phe Arg Leu Ser
            260                 265                 270

Pro Ile Ala Val Thr Met Ser Leu Met Cys Ala Gln Ser Phe Arg Pro
        275                 280                 285

Lys Ala Thr Met Arg Arg Thr Leu Gly Gly Ile Met Val Ala Phe Leu
    290                 295                 300

Asn Ala Tyr Phe Arg Asp Asp Gly Arg Gln Tyr Tyr Ala Ile Ile Ala
305                 310                 315                 320

Asn Arg Ser Leu Ala Pro Thr Asn Leu Phe Ala Glu Lys Lys Gly Phe
                325                 330                 335

Asn Phe Gly Phe Ala Thr Thr Tyr Ala Gln Leu
            340                 345

<210> SEQ ID NO 22
<211> LENGTH: 329
<212> TYPE: PRT
<213> ORGANISM: Citrus sinensis

<400> SEQUENCE: 22

Met Ala Ala Met Val Asp Ala Lys Pro Ala Ala Ser Val Gln Gly Thr
1               5                   10                  15

Pro Leu Leu Ala Thr Ala Thr Leu Pro Val Phe Thr Arg Gly Ile Tyr
            20                  25                  30

Ser Thr Lys Arg Ile Thr Leu Glu Thr Ser Ser Pro Ser Ser Pro Pro
```

```
                35                  40                  45
Pro Pro Lys Pro Leu Ile Ile Val Thr Pro Ala Gly Lys Gly Thr Phe
         50                  55                  60

Asn Val Ile Leu Phe Leu His Gly Thr Ser Leu Ser Asn Lys Ser Tyr
 65                  70                  75                  80

Ser Lys Ile Phe Asp His Ile Ala Ser His Gly Phe Ile Val Val Ala
                 85                  90                  95

Pro Gln Leu Tyr Thr Ser Ile Pro Pro Ser Ala Thr Asn Glu Leu
                100                 105                 110

Asn Ser Ala Ala Glu Val Ala Glu Trp Leu Pro Gln Gly Leu Gln Gln
            115                 120                 125

Asn Leu Pro Glu Asn Thr Glu Ala Asn Val Ser Leu Val Ala Val Met
130                 135                 140

Gly His Ser Arg Gly Gly Gln Thr Ala Phe Ala Leu Ser Leu Arg Tyr
145                 150                 155                 160

Gly Phe Gly Ala Val Ile Gly Leu Asp Pro Val Ala Gly Thr Ser Lys
                165                 170                 175

Thr Thr Gly Leu Asp Pro Ser Ile Leu Ser Phe Asp Ser Phe Asp Phe
                180                 185                 190

Ser Ile Pro Val Thr Val Ile Gly Thr Gly Leu Gly Gly Val Ala Arg
            195                 200                 205

Cys Ile Thr Ala Cys Ala Pro Glu Gly Ala Asn His Glu Glu Phe Phe
210                 215                 220

Asn Arg Cys Lys Asn Ser Ser Arg Ala His Phe Val Ala Thr Asp Tyr
225                 230                 235                 240

Gly His Met Asp Ile Leu Asp Asp Asn Pro Ser Asp Val Lys Ser Trp
                245                 250                 255

Ala Leu Ser Lys Tyr Phe Cys Lys Asn Gly Asn Glu Ser Arg Asp Pro
            260                 265                 270

Met Arg Arg Cys Val Ser Gly Ile Val Val Ala Phe Leu Lys Asp Phe
                275                 280                 285

Phe Tyr Gly Asp Ala Glu Asp Phe Arg Gln Ile Leu Lys Asp Pro Ser
290                 295                 300

Phe Ala Pro Ile Lys Leu Asp Ser Val Glu Tyr Ile Asp Ala Ser Ser
305                 310                 315                 320

Met Leu Thr Thr Thr His Val Lys Val
                325

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:PCR primer
      P1

<400> SEQUENCE: 23
tttcatatgg cagcagcagc acccg                                          25

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence:PCR primer
      P2

<400> SEQUENCE: 24
```

-continued

```
tttctcgagc tgcaatggta cttctgctc                                        29
```

<210> SEQ ID NO 25
<211> LENGTH: 1156
<212> TYPE: DNA
<213> ORGANISM: Triticum aestivum

<400> SEQUENCE: 25

```
gcacgaggcc atctccgcgc tgcttccgct ctagcttcta gctagctaag taagatatgg      60
ctgcaatggc gacgacggtg ttccaggcgg ggccaatgga ggtggatgtg aagcacgtgg     120
acaagagtat gatcccgaac ctggccaggc cgttgatggt ggtggcgccc aaggagaccg     180
gcgcgtaccc cgtcatcgtc ttcctgcacg gctggaacat gctcaacagc tggtacgagc     240
agctcctcac acacgtcgcc tcccatggtt tcatcgccgt cgcaccacag ctctactgga     300
tggtgtccga gcccgatgcg gacgacatag acgccacaaa gcgaatcacc aactggcttg     360
cagatcatga aaggggctc gcccacgtcc tcaaggacgt gctcaaactt gagcatgtcg     420
agcctgacct gtccaagctg gcccctagccg gccatagccg aggcggccag acggccttcg     480
ccgtcgccct gggactaggg gacgccaaga ccaagctgga gctcaagttc tccgccctca     540
tcggcgtcga ccccgtggcc ggggtttcca gagcccaaca gttggagccc aaggtgctca     600
cttttgaacc tgactgtctc gacgtgggga tgccggtgct ggtcatgggg actgggctgg     660
gtcccaagca catcggcgga tttccatgcg ccccggtggg cgtgaaccac gccgaattct     720
acaaggagtg cgcgccgcct cgctaccacc tcgtggtcaa ggactacggg catctcgaca     780
tgctggatga caatgtgccc tatatcatca caactgcat gtgcatgagg aaccaacacg     840
acaccaaaga tcttgctagg aggaccatgg gaggagccat ggttgccttc ctcagggcta     900
aattgcgaat cgatgttcgt gatctcatcg ccatatatca taatcctgag atcgcgccag     960
ccgtcctgga ccaagttgat gagtttcttc cttgcttcgt tggacggcca aatccgtcgt    1020
ctgtgtgaga gttatattac gtgcctatgc ctatctatta ctcctaaata aggtgtgttg    1080
gtgcatggcc ttgtcatggc tcatgactac tatagcacgt ccagtcttcc taattactaa    1140
aaaaaaaaaa aaaaaa                                                    1156
```

<210> SEQ ID NO 26
<211> LENGTH: 323
<212> TYPE: PRT
<213> ORGANISM: Triticum aestivum

<400> SEQUENCE: 26

```
Met Ala Ala Met Ala Thr Thr Val Phe Gln Ala Gly Pro Met Glu Val
  1               5                  10                  15

Asp Val Lys His Val Asp Lys Ser Met Ile Pro Asn Leu Ala Arg Pro
             20                  25                  30

Leu Met Val Ala Pro Lys Glu Thr Gly Ala Tyr Pro Val Ile Val
         35                  40                  45

Phe Leu His Gly Trp Asn Met Leu Asn Ser Trp Tyr Glu Gln Leu Leu
     50                  55                  60

Thr His Val Ala Ser His Gly Phe Ile Ala Val Ala Pro Gln Leu Tyr
 65                  70                  75                  80

Trp Met Val Ser Glu Pro Asp Ala Asp Ile Asp Ala Thr Lys Arg
                 85                  90                  95

Ile Thr Asn Trp Leu Ala Asp His Asp Lys Gly Leu Ala His Val Leu
            100                 105                 110
```

Lys Asp Val Leu Lys Leu Glu His Val Glu Pro Asp Leu Ser Lys Leu
            115                 120                 125

Ala Leu Ala Gly His Ser Arg Gly Gln Thr Ala Phe Ala Val Ala
130                 135                 140

Leu Gly Leu Gly Asp Ala Lys Thr Lys Leu Glu Leu Lys Phe Ser Ala
145                 150                 155                 160

Leu Ile Gly Val Asp Pro Val Ala Gly Val Ser Arg Ala Gln Gln Leu
                165                 170                 175

Glu Pro Lys Val Leu Thr Phe Glu Pro Asp Cys Leu Asp Val Gly Met
            180                 185                 190

Pro Val Leu Val Met Gly Thr Gly Leu Gly Pro Lys His Ile Gly Gly
            195                 200                 205

Phe Pro Cys Ala Pro Val Gly Val Asn His Ala Glu Phe Tyr Lys Glu
        210                 215                 220

Cys Ala Pro Pro Arg Tyr His Leu Val Val Lys Asp Tyr Gly His Leu
225                 230                 235                 240

Asp Met Leu Asp Asp Asn Val Pro Tyr Ile Ile Asn Asn Cys Met Cys
                245                 250                 255

Met Arg Asn Gln His Asp Thr Lys Asp Leu Ala Arg Arg Thr Met Gly
            260                 265                 270

Gly Ala Met Val Ala Phe Leu Arg Ala Lys Leu Arg Ile Asp Val Arg
        275                 280                 285

Asp Leu Ile Ala Ile Tyr His Asn Pro Glu Ile Ala Pro Ala Val Leu
    290                 295                 300

Asp Gln Val Asp Glu Phe Leu Pro Cys Phe Val Gly Arg Pro Asn Pro
305                 310                 315                 320

Ser Ser Val

<210> SEQ ID NO 27
<211> LENGTH: 1274
<212> TYPE: DNA
<213> ORGANISM: Zea mays

<400> SEQUENCE: 27
ccacgcgtcc gccgctactc acgccgtact gtctgatcgg caacacctcg tgtacacgta    60 ggccccggaga tatggcggca tcgccggtgg ccatcggcac ggcggtgttc cagcggggc    120 cactccgcgt ggaggcgagg cacgtcgact acagccaggt ccccagcgtg cccaagccgc    180
tcatggtggt cgcccccacc gacgccggcg tctaccccgt ggccgtcttc ctgcacggct    240
gcaacacggt caacagctgg tatgagagcc tcctgtcgca cgtcgcgtcc acgggttca    300 tcgccgtggc gccccagctc tactgcgtga cgctcaacat gaacgacttg aaggacatcg    360
acgccaccag gcaggtcacc gcctggctcg ccgacaagca gcaaggcctg cgcacgtgc    420 tcgccaacat cctccagctc cacggcgtga ggccggacct ctccaggctg cgctggccg    480 gccacagccg cggcggcgac acggccttcg ccgtggcact cgggctcgga ccgccgcct    540 cggacgacga cgacaacaac gcagacgcag gcacatcgcc ggcggcgttg ccactcaagt    600
tctccgcgct gatcggcgtg accccgtgg cggggctatc caagcaggcg caggtggagc    660
cgaaggtgct gaccttccgg ccccggtccc tcgacccggg gatgccggcg ctggtcgtcg    720
gcacggggct cggccccaag cacgtgggcg ggccgccgtg cgcccccgcg ggcgtcaacc    780
acgccgagtt ctacgacgag tgcgcgccgc cgcggtacca cgtcgtgctg agggactacg    840
ggcacatgga catgctggac gacgcaggcg tgccctacgt catcaacaac tgcatgtgca    900

```
tgaggaacac caaggacacc aaggacctcg ccaggagggc catcggggga gccgtggtgg    960
cgttcctcag ggccacgctg gaggacgacg acgaggatct caaggtcgtg ctcgagaacc   1020
gccctggcct ctcgccggcg gtgctggacc cagttgggca tgacttggct tgaatagcaa   1080
ggctggcgga gtgtgctaca ttgtcgctcc ttatttacac acacatacca catgtttctt   1140
ttccattttg tcctcgatcg tgtcatgtcc cacttgccac aactgtccag tccgctggtg   1200
tccaatgaat agcaaggatg tgaccctaaa aaaaaaaaaa aaaaaaaaaa aaaaaaaaa    1260 aaaaaaaaaa aaag                                                    1274
```

<210> SEQ ID NO 28
<211> LENGTH: 333
<212> TYPE: PRT
<213> ORGANISM: Zea mays

<400> SEQUENCE: 28

```
Met Ala Ala Ser Pro Val Ala Ile Gly Thr Ala Val Phe Gln Arg Gly
 1               5                  10                  15

Pro Leu Arg Val Glu Ala Arg His Val Asp Tyr Ser Gln Val Pro Ser
             20                  25                  30

Val Pro Lys Pro Leu Met Val Val Ala Pro Thr Asp Ala Gly Val Tyr
         35                  40                  45

Pro Val Ala Val Phe Leu His Gly Cys Asn Thr Val Asn Ser Trp Tyr
     50                  55                  60

Glu Ser Leu Leu Ser His Val Ala Ser His Gly Phe Ile Ala Val Ala
 65                  70                  75                  80

Pro Gln Leu Tyr Cys Val Thr Leu Asn Met Asn Asp Leu Lys Asp Ile
                 85                  90                  95

Asp Ala Thr Arg Gln Val Thr Ala Trp Leu Ala Asp Lys Gln Gln Gly
            100                 105                 110

Leu Ala His Val Leu Ala Asn Ile Leu Gln Leu His Gly Val Arg Pro
        115                 120                 125

Asp Leu Ser Arg Leu Ala Leu Ala Gly His Ser Arg Gly Gly Asp Thr
    130                 135                 140

Ala Phe Ala Val Ala Leu Gly Leu Gly Pro Ala Ala Ser Asp Asp Asp
145                 150                 155                 160

Asp Asn Asn Ala Asp Ala Gly Thr Ser Pro Ala Ala Leu Pro Leu Lys
                165                 170                 175

Phe Ser Ala Leu Ile Gly Val Asp Pro Val Ala Gly Leu Ser Lys Gln
            180                 185                 190

Ala Gln Val Glu Pro Lys Val Leu Thr Phe Arg Pro Arg Ser Leu Asp
        195                 200                 205

Pro Gly Met Pro Ala Leu Val Val Gly Thr Gly Leu Gly Pro Lys His
    210                 215                 220

Val Gly Gly Pro Pro Cys Ala Pro Ala Gly Val Asn His Ala Glu Phe
225                 230                 235                 240

Tyr Asp Glu Cys Ala Pro Pro Arg Tyr His Val Val Leu Arg Asp Tyr
                245                 250                 255

Gly His Met Asp Met Leu Asp Asp Gly Val Pro Tyr Val Ile Asn
            260                 265                 270

Asn Cys Met Cys Met Arg Asn Thr Lys Asp Thr Lys Asp Leu Ala Arg
        275                 280                 285

Arg Ala Ile Gly Gly Ala Val Val Ala Phe Leu Arg Ala Thr Leu Glu
    290                 295                 300
```

```
Asp Asp Asp Glu Asp Leu Lys Val Val Leu Glu Asn Arg Pro Gly Leu
305                 310                 315                 320

Ser Pro Ala Val Leu Asp Pro Val Gly His Asp Leu Ala
                325                 330

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence:PCR primer
      P3

<400> SEQUENCE: 29
ttccatggcg gcatcgccgg tggc                                          24

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence:PCR primer
      P4

<400> SEQUENCE: 30
ttgcggccgc cagccttgct attcaagc                                      28
```

CHLOROPHYLLASES

This application claims the benefit of U.S. Provisional Application No. 60/238,161 filed Oct. 5, 2000.

FIELD OF THE INVENTION

This invention is in the field of plant molecular biology. More specifically, this invention pertains to nucleic acid fragments encoding chlorophyllases in plants and seeds.

BACKGROUND OF THE INVENTION

Fruits, stems, and leaves change color in response to developmental and environmental factors. Although these tissues have very different functional, morphological, and biochemical attributes their cells undergo similar changes in ultrastructure and chloroplast composition during fruit ripening and leaf senescence. Chlorophyll breakdown is a primary biochemical event in color changes and the first step in the chlorophyll degradation pathway is catalyzed by chlorophyllase (EC 3.1.1.14). This enzyme catalyzes the hydrolysis of the phytol chain in chlorophylls or pheophytins to produce chlorophyllides or pheophorbides. Chlorophyllases of different mobilities on polyacrylamide gels have been purified from plants and algae and in some instances, like in citrus, there are two chlorophyllase bands present. It is not known what the difference in size represents.

Genes encoding chlorophyllases have been purified from Valencia oranges and *Chenopodium album*. The Valencia orange Chlase1 gene was isolated from a library prepared from mRNA extracted from the fruit peel, stems and leaves. The steady state level of Chlase1 mRNA increased with ethylene treatment (Jacob-Wilk, et al. *Plant J.* (1999) 20:653–661). Although three proteins, of different molecular weight, with chlorophyllase activity have been isolated from *Chenopodium album*, only the gene encoding one of them (CaCLH *C. alum* chlorophyll-chlorophyllido hydrolase) has been identified (Tsuchiya et al. (1999) *Proc. Natl. Acad. Sci. USA* 96:15362–15367). Using sequence similarity to the *C. album* CaCLH chlorophyllase sequence two *Arabidopsis thaliana* genes have also been assigned chlorophyllase activity. Tsuchiya et al. refer to these *Arabidopsis* genes as AtCHL1 and AtCHL2, respectively. Expression of CaCLH, AtCHL1, and AtCHL2 in *E. coli* resulted in chlorophyllase activity (Tsuchiya et al., supra).

The CaCLH deduced amino acid sequence has between 32% and 40% sequence homology with that of AtCHL1 and AtCHL2. All three polypeptides have highly conserved regions that correspond to a conserved motif present in several bacterial, animal, and plant lipases and hydrolases which includes a potential ATP/GTP-binding-site motif, or P-loop. Homology of the entire polypeptide of any of the chlorophyllases with other known lipases is less than 10%.

AtCHL2 was originally labeled COI1 and was isolated from an *Arabidopsis thaliana* mutant (coi1, for coronatine-insensitive 1) which is insensitive to methyl jasmonate (MeJA) and coronatine and produces sterile male flowers. AtCHL1 was originally labeled ATHCOR1 (for *Arabidopsis thaliana* coronatine induced) and was identified as being induced by MeJA, coronatine, and wounding (Benedetti et al. (1998) *Plant Physiol.* 116:1037–1042). Coronatine is a phytotoxin produced by some plant-pathogenic bacteria, and mimics the action of MeJA in plants. MeJA is a plant-signaling molecule involved in stress responses such as wounding and pathogen attack and is essential for pollen grain development in *Arabidopsis thaliana*.

Because of the involvement of chlorophyll degradation in plant cell senescence, identification of cDNAs encoding chlorophyllases in other plants, particularly economically important crop plants, will allow the controlled induction or postponement of senescence.

SUMMARY OF THE INVENTION

The present invention concerns isolated polynucleotides comprising a nucleotide sequence encoding a polypeptide having chlorophyllase activity wherein the amino acid sequence of the polypeptide and the amino acid sequence of SEQ ID NO:2, 4, 6, 8, 10, 12, 14, 16, 18, or 26 have at least 80% sequence identity. It is preferred that the identity be at least 85%, it is preferable if the identity is at least 90%, it is more preferred that the identity be at least 95%. The present invention also relates to isolated polynucleotides comprising the complement of the nucleotide sequence, wherein the complement and the nucleotide sequence contain the same number of nucleotides and are 100% complementary. More specifically, the present invention concerns isolated polynucleotides encoding the polypeptide sequence of SEQ ID NO:2, 4, 6, 8, 10, 12, 14, 16, 18, or 26 or nucleotide sequences comprising the nucleotide sequence of SEQ ID NO:1, 3, 5, 7, 9, 11, 13, 15, 17, or 25.

In a second embodiment, this invention relates to a vector comprising the polynucleotide of the present invention or a recombinant DNA construct comprising the polynucleotide of the present invention operably linked to at least one regulatory sequence.

In a third embodiment, the invention concerns a cell comprising the recombinant DNA construct of the present invention. The cell may be a eukaryotic cell such as a plant cell, or a prokaryotic cell such as a bacterial cell.

In a fourth embodiment, the invention relates to a method of transforming a cell by introducing into the cell a nucleic acid comprising a polynucleotide of the present invention. The invention also concerns a method for producing a plant comprising transforming a plant cell with a nucleic acid molecule comprising a polynucleotide of the present invention and regenerating a plant from the transformed plant cell. In a further embodiment, the seed from the transformed plant is included.

In a fifth embodiment the invention concerns a method for isolating a polypeptide encoded by the polynucleotide of the present invention comprising isolating the polypeptide from a cell transformed with a nucleic acid comprising said polynucleotide.

In a sixth embodiment the invention relates to an isolated chlorophyllase polypeptide comprising an amino acid sequence having a sequence identity of at least 80% when compared to an amino acid sequence having an amino acid sequence of SEQ ID NO:2, 4, 6, 8, 10, 12, 14, 16, 18, or 26. It is preferred that the identity be at least 85%, it is more preferred if the identity is at least 90%, it is preferable that the identity be at least 95%. The invention is related to a polypeptide of SEQ ID NO:2, 4, 6, 8, 10, 12, 14, 16, 18, or 26.

BRIEF DESCRIPTION OF THE DRAWINGS AND SEQUENCE LISTINGS

The invention can be more fully understood from the following detailed description and the accompanying drawings and Sequence Listing which form a part of this application.

FIGS. 1A–1F show a comparison of the amino acid sequences of the grape clone vdb1c.pk002.p19:fis (SEQ ID NO:2), grape clone vrl1c.pk008.o21:fis (SEQ ID NO:4), corn clone csh3c.pk001.a9:fis (SEQ ID NO:6), soybean clone sfl1.pk0046.f8 (SEQ ID NO:8), soybean clone sfl1n1.pk002.m10:fis (SEQ ID NO:10), soybean clone sl2.pk130.f15:fis (SEQ ID NO:12), tulip clone etp1c.pk005.d16:fis (SEQ ID NO:14), wheat clone wl1.pk0012.d7:fis (SEQ ID NO:16), wheat clone wle1n.pk0058.a4:fis (SEQ ID NO:18), wheat clone wyr1c.pk005.f22:fis (SEQ ID NO:26), and the chlorophyllases from *Arabidopsis thaliana* (NCBI General Identifier Nos. 2460203 and 6729677, SEQ ID NO:19 and SEQ ID NO:20, respectively), *Chenopodium album* (NCBI General Identifier No. 6729675, SEQ ID NO:21), and *Citrus sinensis* (NCBI General Identifier No. 7328567, SEQ ID NO:22). Amino acids conserved among all the sequences are indicated by an asterisk (*) above the alignment. The lipase and P-loop motif discussed in Tsuchiya et al. (1999, *Proc. Natl. Acad. Sci. U.S.A.* 96:15362–15367) is underlined and the putative active Serine (from the same article) is written in white and boxed in black. Dashes are used by the program to maximize the alignment. FIG. 1A, amino acids 1 through 70; FIG. 1B, amino acids 71 through 140; FIG. 1C, amino acids 141 through 210; FIG. 1D, amino acids 211–280, FIG. 1E, amino acids 281 through 350; FIG. 1F, amino acids 351 through 397.

FIGS. 2A–2B show a comparison of the amino acid sequences of the corn clone csc1c.pk006.l9:fis (SEQ ID NO:28), and the chlorophyllases from *Arabidopsis thaliana* (NCBI General Identifier Nos. 2460203 and 6729677, SEQ ID NO:19 and SEQ ID NO:20, respectively), *Chenopodium album* (NCBI General Identifier No. 6729675, SEQ ID NO:21), and *Citrus sinensis* (NCBI General Identifier No. 7328567, SEQ ID NO:22). Amino acids conserved among all the sequences are indicated by an asterisk (*) above the alignment. The lipase and P-loop motif discussed in Tsuchiya et al. (1999, *Proc. Natl. Acad. Sci. U.S.A.* 96:15362–15367) is underlined and the putative active Serine (from the same article) is written in white and boxed in black. Dashes are used by the program to maximize the alignment. FIG. 2A, positions 1 through 210; FIG. 2B, positions 211 through 384.

Table 1 lists the chlorophyllase polypeptides that are described herein, the plant species from which the polypeptide is derived, the designation of the cDNA clones that comprise the nucleic acid fragments encoding all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Chlorophyllases

| Species | Clone Designation | SEQ ID NO: (Nucleotide) | SEQ ID NO: (Amino Acid) |
|---|---|---|---|
| Grape | vdb1c.pk002.p19:fis | 1 | 2 |
| Grape | vrl1c.pk008.o21:fis | 3 | 4 |
| Corn | csh3c.pk001.a9:fis | 5 | 6 |
| Soybean | sfl1.pk0046.f8 | 7 | 8 |
| Soybean | sfl1n1.pk002.m10:fis | 9 | 10 |
| Soybean | sl2.pk130.f15:fis | 11 | 12 |

TABLE 1-continued

Chlorophyllases

| Species | Clone Designation | SEQ ID NO: (Nucleotide) | SEQ ID NO: (Amino Acid) |
|---|---|---|---|
| Tulip | etp1c.pk005.d16:fis | 13 | 14 |
| Wheat | wl1.pk0012.d7:fis | 15 | 16 |
| Wheat | wle1n.pk0058.a4:fis | 17 | 18 |
| *A. thaliana* COI1 | GI 2460203 | | 19 |
| *A. thaliana* CLH2 | GI 6729677 | | 20 |
| *C. album* CLH | GI 6729675 | | 21 |
| *C. sinensis* | GI 7328567 | | 22 |
| Oligonucleotide Primer | Primer P1 | 23 | |
| Oligonucleotide Primer | Primer P2 | 24 | |
| Wheat | wyr1c.pk005.f22:fis | 25 | 26 |
| Corn | csc1c.pk006.l9:fis | 27 | 28 |
| Oligonucleotide Primer | Primer P3 | 29 | |
| Oligonucleotide Primer | Primer P4 | 30 | |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. The terms "polynucleotide", "polynucleotide sequence", "nucleic acid sequence", and "nucleic acid fragment"/"isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least 30 contiguous nucleotides, preferably at least 40 contiguous nucleotides, most preferably at least 60 contiguous nucleotides derived from SEQ ID NOs:1, 3, 5, 7, 9, 11, 13, 15, 17, or 25 or the complement of such sequences.

The term "isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

The term "recombinant" means, for example, that a nucleic acid sequence is made by an artificial combination of two otherwise separated segments of sequence, e.g., by chemical synthesis or by the manipulation of isolated nucleic acids by genetic engineering techniques.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate gene silencing or alteration of the functional properties of the resulting protein molecule. It is therefore understood that the invention encompasses more than the specific exemplary nucleotide or amino acid sequences and includes functional equivalents thereof. The terms "substantially similar" and "corresponding substantially" are used interchangeably herein.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least 30 contiguous nucleotides, preferably at least 40 contiguous nucleotides, most preferably at least 60 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by using nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above identities but typically encode a polypeptide having at least 50 amino acids, preferably at least 100 amino acids, more preferably at least 150 amino acids, still more preferably at least 200 amino acids, and most preferably at least 250 amino acids. Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also the explanation of the BLAST alogarithm on the world wide web site for the National Center for Biotechnology Information at the National Library of Medicine of the National Institutes of Health). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to a nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of the nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature.

"Endogenous gene" refers to a native gene in its natural location in the genome of an organism. A "foreign-gene" refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or may be composed of different elements derived from different promoters found in nature, or may even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

"Translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

"3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptides by the cell. "cDNA" refers to DNA that is complementary to and derived from an mRNA template. The cDNA can be single-stranded or converted to double stranded form using, for example, the Klenow fragment of DNA polymerase I. "Sense-RNA" refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single polynucleotide so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

A "protein" or "polypeptide" is a chain of amino acids arranged in a specific order determined by the coding sequence in a polynucleotide encoding the polypeptide. Each protein or polypeptide has a unique function.

"Altered levels" or "altered expression" refers to the production of gene product(s) in transgenic organisms in amounts or proportions that differ from that of normal or non-transformed organisms.

"Mature protein" or the term "mature" when used in describing a protein refers to a post-translationally processed polypeptide; i.e., one from which any pre- or propeptides present in the primary translation product have been removed. "Precursor protein" or the term "precursor" when used in describing a protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference). Thus, isolated polynucleotides of the present invention can be incorporated into recombinant constructs, typically DNA constructs, capable of introduction into and replication in a host cell. Such a construct can be a vector that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., Cloning Vectors: A Laboratory Manual, 1985, supp. 1987; Weissbach and Weissbach, Methods for Plant Molecular Biology, Academic Press, 1989; and Flevin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

"PCR" or "polymerase chain reaction" is well known by those skilled in the art as a technique used for the amplification of specific DNA segments (U.S. Pat. Nos. 4,683,195 and 4,800,159).

Nucleic acid fragments encoding at least a portion of several chlorophyllases have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other chlorophyllases, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, an entire sequence can be used directly to synthesize DNA probes by methods known to the skilled artisan such as random primer DNA labeling, nick translation, end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems, specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least 30 (preferably at least 40, most preferably at least 60) contiguous nucleotides derived from a nucleotide sequence of SEQ ID NO:1, 3, 5, 7, 9, 11, 13, 15, 17, or 25 and the complement of such nucleotide sequences may be used in such methods to obtain a nucleic acid fragment encoding a substantial portion of an amino acid sequence of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

In another embodiment, this invention concerns viruses and host cells comprising either the recombinant DNA fragments of the invention as described herein or an isolated polynucleotide of the invention as described herein.

Examples of host cells which can be used to practice the invention include, but are not limited to, yeast, bacteria, and plants.

As was noted above, the nucleic acid fragments of the instant invention may be used to create transgenic plants in which the disclosed polypeptides are present at higher or lower levels than normal or in cell types or developmental stages in which they are not normally found. This would have the effect of altering the level of chlorophyll in those cells. Manipulation of chlorophyllase activity may be useful for the controlled induction of senescence in agronomic or agricultural applications. For example, expressing a chlorophyllase gene under the control of an inducible promoter will allow plants to mature and age earlier in nurseries, or to mature and age later for their use in florist arrangements or during shipping to retail. Overexpression of chlorophyllase genes in oil-producing crops will result in seeds and extracted oils with reduced chlorophyll-derived pigmentation. Chlorophyllase genes may also be useful to develop male sterility in wheat. It may also be possible to use the chlorophyllase expression as a transformation selection marker where non-transformed tissue will be green and transformed tissue will be non-green. Furthermore, chlorophyllases may be prepared in microbial systems, purified, and added to detergents where they will be used to remove grass and other stains resulting from green plant tissues.

Overexpression of the proteins of the instant invention may be accomplished by first constructing a chimeric gene in which the coding region is operably linked to a promoter capable of directing expression of a gene in the desired tissues at the desired stage of development. The chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Vectors may be constructed comprising the instant isolated polynucleotides or recombinant DNA fragments. The choice of vector is dependent upon the method that will be used to transform host cells. The skilled artisan is well aware of the genetic elements that must be present on the vector in order to successfully transform, select and propagate host cells containing the foreign polynucleotide. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis, among others.

For some applications it may be useful to direct the instant polypeptides to different cellular compartments, or to facilitate their secretion from the cell. It is thus envisioned that the recombinant DNA fragment described above may be further supplemented by directing the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) with or without removing targeting sequences that are already present. While the references cited give examples of each of these, the list is not exhaustive and more targeting signals of use may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of a specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant chlorophyllase polypeptides (or portions thereof) may be produced in heterologous host cells, particularly in the cells of microbial hosts, and can be used to prepare antibodies to these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a recombinant DNA fragment for production of the instant polypeptides. This recombinant DNA fragment could then be introduced into appropriate microorganisms via transformation to provide high level expression of the encoded chlorophyllase. An example of a vector for high level expression of the instant polypeptides in a bacterial host is provided (Example 6).

All or a substantial portion of the polynucleotides of the instant invention may also be used as probes for genetically and physically mapping the genes that they are a part of, and used as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide,* Academic press 1996, pp. 319–346, and references cited therein).

Nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Composition of cDNA Libraries; Isolation and Sequencing of cDNA Clones cDNA libraries representing mRNAs from various grape, corn, soybean, tulip, and wheat tissues were prepared. The characteristics of the libraries are described below.

TABLE 2 cDNA Libraries from Grape, Corn, Soybean, Tulip, and Wheat

| Library | Tissue | Clone |
|---------|--------|-------|
| vdb1c | Grape Developing Bud | vdb1c.pk002.p19:fis |
| vrl1c | Grape Resistant Leaves | vrl1c.pk008.o21:fis |
| csh3c | Corn Shoots and Roots Sprayed With Herbicide* | csh3c.pk001.a9:fis |
| sfl1 | Soybean Immature Flower | sfl1.pk0046.f8 |
| sfl1n1 | Soybean Immature Flower** | sfl1n1.pk002.m10:fis |
| sl2 | Soybean Two-Week-Old Developing Seedlings Treated With 2.5 ppm chlorimuron | sl2.pk130.f15:fis |
| etp1c | Tulip Pistil Developed to 3/4 of its Mature Size | etp1c.pk005.d16:fis |
| wl1 | Wheat Leaf From 7 Day Old Seedling | wl1.pk0012.d7:fis |
| wle1n | Wheat Leaf From 7 Day Old Etiolated Seedling** | wle1n.pk0058.a4:fis |
| wyr1c | Wheat yellow rust infested tissue | wyr1c.pk005.f22:fis |
| csc1c | Corn 20-Day Seedling (Germination Cold Stress). The Seedling Appeared Purple. | csc1c.pk006.l9:fis |

*Application of N-(3,6-dihydro-2H-pyran-4-yl)-4-(3,5-dimethyl-4-isoxazolyl)-4,5-dihydro-N-(1-methylethyl)-5-oxo-1H-tetrazole-1-carboxamide; synthesis and methods of using this compound are described in WO98/35961, incorporated herein by reference.
**These libraries were normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Full-insert sequence (FIS) data is generated utilizing a modified transposition protocol. Clones identified for FIS are recovered from archived glycerol stocks as single colonies, and plasmid DNAs are isolated via alkaline lysis. Isolated DNA templates are reacted with vector primed M13 forward and reverse oligonucleotides in a PCR-based sequencing reaction and loaded onto automated sequencers. Confirmation of clone identification is performed by sequence alignment to the original EST sequence from which the FIS request is made.

Confirmed templates are transposed via the Primer Island transposition kit (PE Applied Biosystems, Foster City, Calif.) which is based upon the *Saccharomyces cerevisiae* Ty1 transposable element (Devine and Boeke (1994) *Nucleic Acids Res.* 22:3765–3772). The in vitro transposition system places unique binding sites randomly throughout a population of large DNA molecules. The transposed DNA is then used to transform DH10B electro-competent cells (Gibco BRL/Life Technologies, Rockville, Md.) via electroporation. The transposable element contains an additional selectable marker (named DHFR; Fling and Richards (1983) *Nucleic Acids Res.* 11:5147–5158), allowing for dual selection on agar plates of only those subclones containing the integrated transposon. Multiple subclones are randomly selected from each transposition reaction, plasmid DNAs are prepared via alkaline lysis, and templates are sequenced (ABI Prism dye-terminator ReadyReaction mix) outward from the transposition event site, utilizing unique primers specific to the binding sites within the transposon.

Sequence data is collected (ABI Prism Collections) and assembled using Phred/Phrap (P. Green, University of Washington, Seattle). Phrep/Phrap is a public domain software program which re-reads the ABI sequence data, re-calls the bases, assigns quality values, and writes the base calls and quality values into editable output files. The Phrap sequence assembly program uses these quality values to increase the accuracy of the assembled sequence contigs. Assemblies are viewed by the Consed sequence editor (D. Gordon, University of Washington, Seattle).

In some of the clones the cDNA fragment corresponds to a portion of the 3'-terminus of the gene and does not cover the entire open reading frame. In order to obtain the upstream information one of two different protocols are used. The first of these methods results in the production of a fragment of DNA containing a portion of the desired gene sequence while the second method results in the production of a fragment containing the entire open reading frame. Both of these methods use two rounds of PCR amplification to obtain fragments from one or more libraries. The libraries some times are chosen based on previous knowledge that the specific gene should be found in a certain tissue and some times are randomly-chosen. Reactions to obtain the same gene may be performed on several libraries in parallel or on a pool of libraries. Library pools are normally prepared using from 3 to 5 different libraries and normalized to a uniform dilution. In the first round of amplification both methods use a vector-specific (forward) primer corresponding to a portion of the vector located at the 5'-terminus of the clone coupled with a gene-specific (reverse) primer. The first method uses a sequence that is complementary to a portion of the already known gene sequence while the second method uses a gene-specific primer complementary to a portion of the 3'-untranslated region (also referred to as UTR). In the second round of amplification a nested set of primers is used for both methods. The resulting DNA fragment is ligated into a pBluescript vector using a commercial kit and following the manufacturer's protocol. This kit is selected from many available from several vendors including Invitrogen (Carlsbad, Calif.), Promega Biotech (Madison, Wis.), and Gibco-BRL (Gaithersburg, Md.). The plasmid DNA is isolated by alkaline lysis method and submitted for sequencing and assembly using Phred/Phrap, as above.

Example 2

Identification of cDNA Clones cDNA clones encoding chlorophyllases were identified by conducting BLAST (Basic Local Alignment Search Tool; Altschul et al. (1993) *J. Mol. Biol.* 215:403–410; see also the explanation of the BLAST algorithm on the world wide web site for the National Center for Biotechnology Information at the National Library of Medicine of the National Institutes of Health) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

ESTs submitted for analysis are compared to the genbank database as described above. ESTs that contain sequences more 5- or 3-prime can be found by using the BLASTn algorithm (Altschul et al (1997) *Nucleic Acids Res.* 25:3389–3402) against the Du Pont proprietary database comparing nucleotide sequences that share common or overlapping regions of sequence homology. Where common or overlapping sequences exist between two or more nucleic acid fragments, the sequences can be assembled into a single contiguous nucleotide sequence, thus extending the original fragment in either the 5 or 3 prime direction. Once the most 5-prime EST is identified, its complete sequence can be determined by Full Insert Sequencing as described in Example 1. Homologous genes belonging to different species can be found by comparing the amino acid sequence of a known gene (from either a proprietary source or a public database) against an EST database using the tBLASTn algorithm. The tBLASTn algorithm searches an amino acid query against a nucleotide database that is translated in all 6 reading frames. This search allows for differences in nucleotide codon usage between different species, and for codon degeneracy.

Example 3

Characterization of cDNA Clones Encoding Chlorophyllases

The BLASTX search using the EST sequences from clones listed in Table 3 revealed similarity of the polypeptides encoded by the cDNAs to chlorophyllases from *Arabidopsis thaliana* (NCBI General Identifier No. 2460203 and 6729677), *Chenopodium album* (NCBI General Identifier No. 6729675), and *Citrus sinensis* (NCBI General Identifier No. 7328567). Shown in Table 3 are the BLAST results for the sequences of the entire cDNA inserts comprising the indicated cDNA clones ("FIS") or for the sequences of FISs encoding entire chlorophyllases ("CGS"):

TABLE 3

BLAST Results for Sequences Encoding Polypeptides Homologous to Chlorophyllase

| Clone | Status | BLAST pLog Score | | | |
|---|---|---|---|---|---|
| | | 2460203 | 6729677 | 6729675 | 7328567 |
| vdb1c.pk002.p19:fis | FIS | 78.22 | 75.30 | 64.52 | 74.70 |
| vrl1c.pk008.o21:fis | FIS | 67.15 | 113.00 | 49.52 | 61.52 |
| csh3c.pk001.a9:fis | CGS | 54.30 | 78.40 | 45.70 | 53.70 |
| sfl1.pk0046.f8 | CGS | 78.00 | 68.40 | 59.00 | na |
| sfl1n1.pk002.m10:fis | CGS | 80.04 | 66.40 | 62.10 | 66.30 |
| sl2.pk130.f15:fis | CGS | 76.30 | 69.30 | 60.10 | 66.70 |
| etp1c.pk005.d16:fis | CGS | 65.52 | 87.40 | 52.10 | 62.40 |
| wl1.pk0012.d7:fis | FIS | 38.30 | 35.40 | 35.00 | 31.00 |
| wle1n.pk0058.a4:fis | CGS | 76.00 | 68.00 | 55.40 | 61.04 |
| wyr1c.pk005.f22:fis | CGS | 54.40 | 56.10 | 51.10 | 49.00 |

The nucleotide sequence from the entire cDNA insert in clone vdb1c.pk002.p19:fis is shown in SEQ ID NO:1. Nucleotides 1 through 855 from SEQ ID NO:1 encode the amino acid sequence of SEQ ID NO:2. The nucleotide sequence from the entire cDNA insert in clone vrl1c.pk008.o21:fis is shown in SEQ ID NO:3. Nucleotides 1 through 933 from SEQ ID NO:3 encode the amino acid sequence of SEQ ID NO:4. The nucleotide sequence from the entire cDNA insert in clone csh3c.pk001.a9:fis is shown in SEQ ID NO:5 and it encodes an entire corn chlorophyllase. Nucleotides 71 through 1106 from SEQ ID NO:5 encode the amino acid sequence of SEQ ID NO:6 with nucleotides 107–109 corresponding to a stop codon. The nucleotide sequence from the entire cDNA insert in clone sfl1.pk0046.f8 is shown in SEQ ID NO:7 and it encodes an entire soybean chlorophyllase. Nucleotides 12 through 953 from SEQ ID NO:7 encode the amino acid sequence of SEQ ID NO:8 with nucleotides 954–956 corresponding to a stop codon. The nucleotide sequence from the entire cDNA insert in clone sfl1n1.pk002.m10:fis is shown in SEQ ID NO:9 and it encodes an entire soybean chlorophyllase. Nucleotides 26 through 964 from SEQ ID NO:9 encode the amino acid sequence of SEQ ID NO:10 with nucleotides 965–967 corresponding to the stop codon. The nucleotide sequence from the entire cDNA insert in clone sl2.pk130.f15:fis is shown in SEQ ID NO:11 and it encodes an entire soybean chlorophyllase. Nucleotides 42 through 989 from SEQ ID NO:11 encode the amino acid sequence of SEQ ID NO:12 with nucleotides 990–992 corresponding to the stop codon. The nucleotide sequence from the entire cDNA insert in clone etp1c.pk005.d16:fis is shown in SEQ ID NO:13 and it encodes an entire tulip chlorophyllase. Nucleotides 97 through 1104 from SEQ ID NO:13 encode the amino acid sequence of SEQ ID NO:14 with nucleotides 1105–1107 corresponding to the stop codon. The nucleotide sequence from the entire cDNA insert in clone wl1.pk0012.d7:fis is shown in SEQ ID NO:15. Nucleotides 1 through 615 from SEQ ID NO:15 encode the amino acid sequence of SEQ ID NO:16 with nucleotides 616–618 corresponding to the stop codon. The nucleotide sequence from the entire cDNA insert in clone wle1n.pk0058.a4:fis is shown in SEQ ID NO:17 and it encodes an entire wheat chlorophyllase. Nucleotides 47 through 1003 from SEQ ID NO:17 encode the amino acid sequence of SEQ ID NO:18 with nucleotides 1004–1006 corresponding to the stop codon. The nucleotide sequence from the entire cDNA insert in clone wyr1c.pk005.f22:fis is shown in SEQ ID NO:25 and it encodes an entire wheat chlorophyllase. Nucleotides 57 through 1025 from SEQ ID NO:25 encode the amino acid sequence of SEQ ID NO:26 with nucleotides 1026–1028 corresponding to the stop codon.

Nucleotides 286 through 669 from soybean clone sfl1.pk0046.f8 are 98% identical to nucleotides 6 through 390 of an EST found in the NCBI database having gi No. 6135059. Nucleotides 24 through 299 from soybean clone sl2.pk130.f15:fis are 100% identical to nucleotides 1 through 276 of an EST found in the NCBI database having gi No. 7284173. Nucleotides 865 through 1101 from soybean clone sl2.pk130.f15:fis are 100% identical to nucleotides 18 through 254 of an EST found in the NCBI database having gi No. 6914327. The three EST sequences mentioned above and found in the NCBI database are identified as having similarities with the coronatine induced protein 1.

FIGS. 1A–1F present an alignment of the amino acid sequences set forth in SEQ ID NOs:2, 4, 6, 8, 10, 12, 14, 16, 18, and 26 with the AtCHL1 sequence (SEQ ID NO:19), CaCHL sequence (SEQ ID NO:21), AtCHL2 sequence (SEQ ID NO:20), and the *Citrus sinensis* chlorophyllase sequence (SEQ ID NO:22). The lipase and P-loop motif discussed in Tsuchiya et al. (1999, *Proc. Natl. Acad. Sci. U.S.A.* 96:15362–15367) is underlined and the putative active Serine is written in white and boxed in black. As can be seen in these figures, the amino acid sequences of SEQ ID NO:2, 4, 6, 8, 10, 12, 14, 16, 18, and 26 have a conserved motif comprising (Leu/Ile)-(Ser/Val/Ala)-Gly-His-Ser-(Arg/Lys)-Gly-Gly-(Lys/Gln)-(Thr/Val/Asp)-(Ala/Val)-Phe-(Ala/Ser)-(Leu/Val)-Ala-Leu which includes the putative active Serine.

The data in Table 4 presents the percent identity of the amino acid sequences set forth in SEQ ID NOs:2, 4, 6, 8, 10, 12, 14, 16, 18, and 26, with the AtCHL1 sequence (NCBI General Identifier No. 2460203, SEQ ID NO:19), the CaCHL sequence (NCBI General Identifier No. 6729675, SEQ ID NO:21), the AtCHL2 sequence (NCBI General Identifier No. 6729677, SEQ ID NO:20), and the *Citrus sinensis* chlorophyllase sequence (NCBI General Identifier No. 7328567, SEQ ID NO:22).

TABLE 4

Percent Identity of Amino Acid Sequences Deduced From the Nucleotide Sequences of cDNA Clones Encoding Polypeptides Homologous to Chlorophyllases

| Clone | SEQ ID NO. | Percent Identity to | | | |
|---|---|---|---|---|---|
| | | 2460203 | 6729677 | 7328567 | 6729675 |
| vdb1c.pk002.p19:fis | 2 | 49.1 | 48.4 | 45.6 | 43.5 |
| vrl1c.pk008.o21:fis | 4 | 40.5 | 58.8 | 36.0 | 32.5 |
| csh3c.pk001.a9:fis | 6 | 32.7 | 44.0 | 32.2 | 29.5 |
| sfl1.pk0046.f8 | 8 | 42.5 | 38.4 | 40.0 | 36.8 |
| sfl1n1.pk002.m10:fis | 10 | 44.7 | 39.6 | 39.9 | 38.0 |
| sl2.pk130.f15:fis | 12 | 43.4 | 39.0 | 40.8 | 36.7 |
| etp1c.pk005.d16:fis | 14 | 39.2 | 47.5 | 35.0 | 33.9 |
| wl1.pk0012.d7:fis | 16 | 36.6 | 36.6 | 33.7 | 38.0 |
| wle1n.pk0058.a4:fis | 18 | 42.0 | 38.4 | 37.3 | 33.9 |
| wyr1c.pk005.f22:fis | 26 | 31.1 | 34.3 | 31.0 | 32.8 |

Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode one entire corn, three entire soybean, one entire tulip, one entire wheat, and a substantial portion of two grape and one wheat chlorophyllases. These are the first corn, soybean, tulip, wheat, and grape sequences known to Applicant to encode chlorophyllases.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf (+) (Promega). Vector and insert DNA can be ligated at 15° C. overnight, essentially as described (Maniatis). The ligated DNA may then be used to transform *E. coli* XL1-Blue (Epicurian Coli XL-1 Blue®; Stratagene). Bacterial transformants can be screened by restriction enzyme digestion of plasmid DNA and limited nucleotide sequence analysis using the dideoxy chain termination method (Sequenase® DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains bialophos (5 mg per liter) and lacks casein or proline. The tissue continues to grow slowly on this medium. After an additional 2 weeks the tissue can be transferred to fresh N6 medium containing bialophos. After 6 weeks, areas of about 1 cm in diameter of actively growing callus can be identified on some of the plates containing the bialophos-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites NcoI (which includes the ATG translation initiation codon), SmaI, KpnI and XbaI. The entire cassette is flanked by HindIII sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can be maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic® PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μL spermidine (0.1 M), and 50 μL $CaCl_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoRI and HindIII sites in pET-3a at their original positions. An oligonucleotide adaptor containing EcoRI and HindIII sites was inserted at the BamHI site of pET-3a. This created pET-3aM with additional unique cloning sites for insertion of genes into the expression vector. Then, the NdeI site at the position of translation initiation was converted to an NcoI site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% low melting agarose gel. Buffer and agarose contain 10 µg/ml ethidium bromide for visualization of the DNA fragment. The fragment can then be purified from the agarose gel by digestion with GELase™ (Epicentre Technologies, Madison, Wis.) according to the manufacturer's instructions, ethanol precipitated, dried and resuspended in 20 µL of water. Appropriate oligonucleotide adapters may be ligated to the fragment using T4 DNA ligase (New England Biolabs (NEB), Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21(DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Determination of Chlorophyllase Activity in Clone wle1n.pk0058.a4

To establish its functional identity, the cDNA insert in clone wle1n.pk0058.a4 was expressed in bacteria and assayed for chlorophyllase activity. Initially, the entire cDNA insert in clone wle1n.pk0058.a4 was amplified by PCR using Pfu polymerase (Stratagene) and the oligonucleotide primers P1 (sense, SEQ ID NO:23) and P2 (antisense, SEQ ID NO:24):

```
P1:
5'-TTTCATATGGCAGCAGCAGCACCCG-3'       (SEQ ID NO:23)

P2:
5'-TTTCTCGAGCTGCAATGGTACTTCTGCTC-3'.  (SEQ ID NO:24)
```

The amplified fragment was cloned into pCR-Script Amp SK(+) (Stratagene) according to the manufacturer's protocol. The resulting plasmid was digested with NdeI and XhoI and the fragment corresponding to the cDNA insert from clone wle1n.pk0058.a4 was purified and inserted into the corresponding sites of the *E. coli* expression vector pET24a (Novagen). The resulting plasmid containing the cDNA insert from clone wle1n.pk0058.a4 in the pET24a vector was named pWhtCHL.

Recombinant protein was produced by expression of pWhtCHL in the *E. coli* strain BL21(DE3). A 35 mL culture of cells harboring pWhtCHL was grown in LB media to an absorbance at 600 nm of 0.5 and induction of the recombinant protein was accomplished by addition of IPTG to a final concentration of 0.4 mM. The cells were grown for an additional 4 hours and harvested by centrifugation. To obtain a crude protein extract, cells were resuspended in 3 mL of lysis buffer (50 mM Tris-HCl (pH7.5), 38 µM octylglucoside, and 1 mM PMSF [phenylmethanesulfonyl fluoride]). The cells were then lysed using a French pressure cell. The protein content in the resulting crude extract was determined according to the method of Bradford (Bradford, M. M. (1976) *Anal. Biochem.* 72: 248–254). Separation of this extract by SDS-polyacrylamide gel electrophoresis and staining with coomasie revealed the presence of a strongly-expressed polypeptide of approximately 35 kDa that was absent from extracts of induced cells harboring the pET24a vector without insert. This 35 kDa induced protein corresponds to the size expected for a polypeptide derived from the cDNA insert in clone wle1n.pk0058.a4.

The chlorophyllase activity assay was modified from that described by Tsuchiya et al. (1997) *Plant Cell Physiol.* 40:104–108). The protein concentration varied depending on whether the assay was done on the vector control or the samples expressing the chlorophyllase. Considerably less protein from the chlorophyllase samples was used because the activity was much, much greater than that in the vector control. Extracts from *E. coli* expressing the wheat chlorophyllase contained 0.14 µg of protein while extracts from *E. coli* containing the vector alone contained 10.5 µg of protein. Reactions were conducted in a total volume of 0.5 mL, consisting of 0.4 mL of crude protein prepared above diluted in the lysis buffer and 0.1 mL of a crude chlorophyll extract dissolved in acetone. The concentration of chlorophyll a in the extract was 0.88 µM. The assay was conducted for 5 min with rapid shaking (285 rpm) in order to insure that the acetone phase was dispersed in the reaction buffer. The reaction was stopped with the addition of 1.5 mL of acetone:

hexane (1:2, v/v) and 0.5 mL of 2M Tris (pH9.0). After shaking the reaction tubes to homogenization, the organic and aqueous phases were partitioned by centrifugating the tubes at 2500×g for 10 minutes. The aqueous phase containing the chlorophyllide a reaction product was recovered, and its absorbance was measured at 667 nm. The amount of chlorophyllide a generated in the assay was determined using the extinction coefficient 76.79 $mM^{-1}cm^{-1}$.

From assays conducted as described above, chlorophyllase activity was found to be nearly 900-fold greater in crude extracts of *E. coli* expressing pWhtCHL than in extracts from *E. coli* expressing the pET24a vector without insert. These results are thus consistent with the functional identification of the cDNA insert in clone wle1n.pk0058.a4 as encoding a chlorophyllase.

Example 8

Identification of a Corn Clone Encoding a Different Chlorophyllase Isozyme

The BLASTX search using the EST sequences from clone csc1c.pk006.l9:fis revealed similarity of the polypeptides encoded by the cDNAs to chlorophyllases from *Arabidopsis thaliana* (NCBI General Identifier No. 2460203 and 6729677), *Chenopodium album* (NCBI General Identifier No. 6729675), and *Citrus sinensis* (NCBI General Identifier No. 7328567). Shown in Table 5 are the BLAST results for the sequences of the entire cDNA insert comprising the indicated cDNA clone and encoding entire chlorophyllase ("CGS"):

TABLE 5

BLAST Results for Sequences Encoding Polypeptides Homologous to Chlorophyllase

| Clone | Status | BLAST pLog Score | | | |
|---|---|---|---|---|---|
| | | 2460203 | 6729677 | 6729675 | 7328567 |
| csc1c.pk006.l9:fis | CGS | 55.15 | 54.30 | 47.15 | 45.52 |

The nucleotide sequence from the entire cDNA insert in clone csc1c.pk006.l9:fis is shown in SEQ ID NO:27 and it encodes an entire corn chlorophyllase. Nucleotides 72 through 1069 from SEQ ID NO:27 encode the amino acid sequence of SEQ ID NO:28 with nucleotides 1070–1072 corresponding to the stop codon. When this corn chlorophyllase is compared with other chlorophyllases it shows an amino acid insertion close to the N-terminus of the protein.

FIGS. 2A–2B present an alignment of the amino acid sequences set forth in SEQ ID NO:28 with the AtCHL1 sequence (SEQ ID NO:19), CaCHL sequence (SEQ ID NO:21), AtCHL2 sequence (SEQ ID NO:20), and the *Citrus sinensis* chlorophyllase sequence (SEQ ID NO:22). The lipase and P-loop motifs discussed in Tsuchiya et al. (1999, *Proc. Natl. Acad. Sci. U.S.A.* 96:15362–15367) are underlined and the putative active Serine is written in white and boxed in black. Amino acids identical among all the sequences in the alignment are indicated by an asterisk (*) above the alignment. As can be seen in the figure, the amino acid sequence of SEQ ID NO:28 contains a motif containing Leu-Ala-Gly-His-Ser-Arg-Gly-Gly-Asp-Thr-Ala-Phe-Ala-Val-Ala-Leu which includes the putative active Serine.

The data in Table 6 presents the percent identity of the amino acid sequences set forth in SEQ ID NO:28, with the AtCHL1 sequence (NCBI General Identifier No. 2460203, SEQ ID NO:21), the CaCHL sequence (NCBI General Identifier No. 6729675, SEQ ID NO:22), the AtCHL2 sequence (NCBI General Identifier No. 6729677, SEQ ID NO:20), and the *Citrus sinensis* chlorophyllase sequence (NCBI General Identifier No. 7328567, SEQ ID NO:22).

TABLE 6

Percent Identity of Amino Acid Sequences Deduced From the Nucleotide Sequences of cDNA Clones Encoding Polypeptides Homologous to Chlorophyllase

| Clone | SEQ ID NO. | Percent Identity to | | | |
|---|---|---|---|---|---|
| | | 2460203 | 6729677 | 7328567 | 6729675 |
| csc1c.pk006.l9:fis | 28 | 34.0 | 34.3 | 28.9 | 29.1 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

To determine if the insert in clone csc1c.pk006.l9:fis encodes an active chlorophyllase, the encoded polypeptide was expressed in *E. coli* and tested for chlorophyllase activity using essentially the method described in Example 7.

Initially, the chlorophyllase-coding sequence in clone csc1c.pk006.19 was amplified by PCR using Pfu polymerase (Stratagene) and the oligonucleotide primers P3 (sense, SEQ ID NO:29) and P4 (antisense, SEQ ID NO:30):

P3:
5'-TTCCATGGCGGCATCGCCGGTGGC-3'   (SEQ ID NO:29)

P4:
5'-TTGCGGCCGCCAGCCTTGCTATTCAAGC-3'   (SEQ ID NO:30)

The amplified DNA fragment was cloned into pCR-Script Amp SK(+) (Stratagene) according to the manufacturer's protocol. The resulting plasmid was digested with NcoI and NotI and the fragment corresponding to the chlorophyllase-cloning region of clone csc1c.pk006.l9:fis was purified and inserted into NcoI/NotI-cut *E. coli* expression vector pET24a (Novagen) to generate the plasmid pZmCHL.

Expression of the protein encoded by clone pZmCHL, its purification, and measurement of chlorophyllase activity will be as described in Example 7.

Sequence alignments, BLAST scores and probabilities, and chlorophyllase activity assays indicate that the nucleic acid fragment comprising the instant cDNA clone encodes one entire corn chlorophyllase isozyme of a class not previously known to Applicant.

What is claimed is:

1. An isolated polynucleotide comprising:
   (a) a nucleotide sequence encoding a polypeptide having chlorophyllase activity, wherein the amino acid sequence of the polypeptide and the amino acid sequence of SEQ ID NO:18 have at least 80% sequence identity, or
   (b) the complement of the nucleotide sequence, wherein the complement and the nucleotide sequence contain the same number of nucleotides and are 100% complementary.

2. The polynucleotide of claim 1 wherein the sequence identity is at least 90% of amino acid.

3. The polynucleotide of claim 1 wherein the sequence identity is at least 95% of amino acid.

4. The polynucleotide of claim 1 wherein the polynucleotide encodes the polypeptide sequence of SEQ ID NO:18.

5. The polynucleotide of claim 1 wherein the nucleotide sequence comprises the nucleotide sequence of SEQ ID NO:17.

6. A vector comprising the polynucleotide of claim 1.

7. A recombinant DNA construct comprising the polynucleotide of claim 1 operably linked to at least one regulatory sequence.

8. A cell comprising the recombinant DNA construct of claim 7.

9. The cell of claim 8 wherein the cell is a plant cell or a bacterial cell.

10. A method for producing a plant comprising transforming a plant cell with the polynucleotide of claim 1 and regenerating a plant from the transformed plant cell.

11. A plant comprising the recombinant DNA construct of claim 7.

12. A seed comprising the recombinant DNA construct of claim 7.

13. A method for transforming a cell, comprising introducing into a cell the polynucleotide of claim 1.

14. A method for isolating a polypeptide encoded by the polynucleotide of claim 1 comprising isolating the polypeptide from a cell transformed with said polynucleotide.

* * * * *

UNITED STATES PATENT AND TRADEMARK OFFICE
CERTIFICATE OF CORRECTION

| | | |
|---|---|---|
| PATENT NO. | : 7,199,284 B2 | Page 1 of 1 |
| APPLICATION NO. | : 10/381123 | |
| DATED | : April 3, 2007 | |
| INVENTOR(S) | : Edgar B. Cahoon, Rebecca E. Cahoon and Catherine J. Thorpe | |

It is certified that error appears in the above-identified patent and that said Letters Patent is hereby corrected as shown below:

Lage page of patent, Claims section, Claim 2, line 44, preceeding "amino acid" insert --the--.

Lage page of patent, Claims section, Claim 3, line 46, preceeding "amino acid" insert --the--.

Signed and Sealed this

Nineteenth Day of June, 2007

JON W. DUDAS
*Director of the United States Patent and Trademark Office*